(12) United States Patent
Dotan et al.

(10) Patent No.: US 7,906,291 B2
(45) Date of Patent: *Mar. 15, 2011

(54) METHOD FOR DIAGNOSING MULTIPLE SCLEROSIS

(75) Inventors: Nir Dotan, Shoham (IL); Avinoam Dukler, Moddi'in (IL)

(73) Assignee: Glycominds Ltd., Lod (IL)

( * ) Notice: Subject to any disclaimer, the term of this patent is extended or adjusted under 35 U.S.C. 154(b) by 449 days.

This patent is subject to a terminal disclaimer.

(21) Appl. No.: 11/345,190

(22) Filed: Jan. 31, 2006

(65) Prior Publication Data

US 2006/0234301 A1    Oct. 19, 2006

(51) Int. Cl.
    *G01N 33/53* (2006.01)
(52) U.S. Cl. ...................................................... 435/7.1
(58) Field of Classification Search ........................ None
    See application file for complete search history.

(56) References Cited

U.S. PATENT DOCUMENTS

| | | | | |
|---|---|---|---|---|
| 5,030,560 | A | 7/1991 | Sinor et al. | 435/7.21 |
| 6,972,172 | B2 | 12/2005 | Dukler et al. | 435/6 |
| 7,537,900 | B2 | 5/2009 | Dotan et al. | 435/7.1 |
| 7,572,592 | B2 | 8/2009 | Dotan et al. | |
| 2004/0077023 | A1 | 4/2004 | Dotan et al. | 435/7.2 |
| 2004/0241763 | A1 | 12/2004 | Dotan et al. | 435/7.2 |
| 2006/0172338 | A1 | 8/2006 | Dotan et al. | 435/7.1 |
| 2006/0234301 | A1 | 10/2006 | Dotan et al. | |

FOREIGN PATENT DOCUMENTS

| | | |
|---|---|---|
| WO | WO 00/49412 | 8/2000 |
| WO | WO 01/14881 A1 | 3/2001 |
| WO | WO 01/51207 A1 | 7/2001 |
| WO | WO 02/18950 A1 | 3/2002 |
| WO | WO 02/064556 A2 | 8/2002 |
| WO | WO 03/000733 A2 | 1/2003 |
| WO | WO 2004/015420 A1 | 2/2004 |
| WO | WO-2004034031 A2 | 4/2004 |

OTHER PUBLICATIONS

Bao *J. Chromatogr. B.*, 699(1+2):463-480 (1997).
Berger et al. *N. Engl. J. Med.*, 349:139-145 (2003).
Bozzaro et al. *Cell Differentiation*, 17:83-94 (1985).
Brex et al. *N. Engl. J. Med.*, 346(3):158-164 (2002).
Carotenuto et al. *J. Med. Chem.*, 44:2378-2381 (2001).
Comi et al. *Lancet*, 357:1576-1582 (2001).
Holme et al. *Carbohydr. Res.*, 8:43-55 (1968).
Hou et al. *J. Immunol.*, 170:4373-4379 (2003).
Jacobs et al. *Ann. Neurol.*, 41(3):392-398 (1997).
Jacobs et al. *N. Engl. J. Med.*, 343(13):898-904 (2000).
Kurtzke *Neurol.*, 33(11):1444-1452 (1983).
Matsuda et al. *Mol. Immun.*, 24(5):421-425 (1987).
McDonald et al. *Ann. Neurol.*, 50(1):121-127 (2001).
O'Riordan et al. *Brain*, 121:495-503 (1998).
Papini et al. *Proceedings of the 10th International Congress of Immunology*, Monduzzi Editore, pp. 1239-1244 (1998).
Poser et al. *Ann. Neurol.*, 13(3):227-231 (1983).
Rongen et al. *J. Immunol. Meth.*, 204(2):105-133 (1997).
Saveliev et al. *Immun. Letters*, 86:291-297 (2003).
Schmalzing et al. *Electrophoresis*, 18(12-13):2184-2193 (1997).
Schwarz et al. *Glycobiol.*, 13(11):749-754 (2003).
Self et al. *Curr. Opin. Biotechnol.*, 7:60-65 (1996).
Weinshenker et al. *Brain*, 112(part VI):1419-1428 (1989).
Zhan et al. *Biochem. Biophys. Res. Commun.*, 308(1):12-22 (2003).
Mazzucco, S., et al. Bioorg. Med. Chem. Letters (1999) 9:167-172.
Schwarz, M., et al., J. Neuro. Sci. (2006) 244:59-68.
Alberts et al., "Sugars Are Food Molecules of the Cell", in *Molecular Biology of the Cell*, Garland Publishing Inc., New York & London, pp. 50-51 (1983).
Stryer, L., *Biochemistry*, 4th Edition, W.H. Freeman and Company, New York, NY, pp. 472-473 (1995).
Banin et al., "A Novel Linear Code® Nomenclature for Complex Carbohydrates", *Trends Glycoscience Glycotech.*, 14(77):127-137 (2002).
Bergamaschi, R., "Prognostic Factors in Multiples Sclerosis", *Int. Rev. Neurobiol.*, 79:423-447 (2007).
Binder et al., "The role of natural antibodies in atherogenesis", *J. Lipid Res.*, 46:1353-1363 (2005).
Boneschi et al., "Mitoxantrone for multiple sclerosis (Review)", *Cochrane Database of Systematic Rev.*, John Wiley & Sons, 4:CD002127 (2005).
Brusaferri et al., "Steroids for multiple sclerosis and optic neuritis: a meta-analysis of randomized controlled clinical trials", *J. Neurol.*, 247(6):435-442 (2000).
Confavreux et al., "Early clinical predictors and progression of irreversible disability in multiple sclerosis: an amnesic process", *Brain*, 126:770-782 (2003).
Dalton et al., "Application of the new McDonald Criteria to Patients with Clinically Isolated Syndromes Suggestive of Multiple Sclerosis", *Ann. Neurol.*, 52:47-53 (2002).
Dotan et al., "Anti-glycan antibodies as biomarkers for diagnosis and prognosis", *Lupus*, 15(7):442-450 (2006).
Dovio et al., "Immediate Fall of Bone Formation and Transient Increase of Bone Resorption in the Course of High-Dose, Short-Term Glucocorticoid Therapy in Young Patients with Multiple Sclerosis", *J. Clin. Endocrinol. Metab.*, 89(10):4923-4928 (2004).
Durelli et al., "MRI activity and neutralising antibody as predictors of response to interferon β treatment in multiple sclerosis", *J. Neurol. Neurosurg. Psychiatry*, 79:646-651 (2008).
Felici et al., "Phage-Displayed Peptides as Tools for Characterization of Human Sera", *Meth. Enzymol.*, 267:116-129 (1996).
Fisniku et al., "Disability and $T_2$ MRI lesions: a 20-year follow-up of patients with relapse onset of multiple sclerosis", *Brain*, 131:808-817 (2008).
Freedman et al., "Anti-α-glucose-based glycan IgM antibodies predict relapse activity in multiple sclerosis after the first neurological event", *Multiple Sclerosis*, 15(4):422-430 (2009).

(Continued)

*Primary Examiner* — G. R Ewoldt
(74) *Attorney, Agent, or Firm* — Mintz, Levin, Cohn, Ferris, Glovsky and Popeo, P.C.

(57) ABSTRACT

Disclosed is a method for diagnosing multiple sclerosis and more particularly to a method for diagnosing multiple sclerosis by measuring levels of antibodies to glycans in a biological sample.

10 Claims, 6 Drawing Sheets

OTHER PUBLICATIONS

Freedman et al., "Recommended Standard of Cerebrospinal Fluid Analysis in the Diagnosis of Multiple Sclerosis", *Arch. Neurol.*, 62:865-870 (2005).

Gonsette, R.E., "Compared benefit of approved and experimental immunosuppressive therapeutic approaches in multiple sclerosis", *Exp. Opin. Pharmacother.*, 8(8):1103-1116 (2007).

Gyorgy et al., "Natural autoantibodies reactive with glycosaminoglycans in rheumatoid arthritis", *Arthritis Res. Ther.*, 10(5):1-12 (2008).

Johnson, K.P., "Control of multiple sclerosis relapses with immunomodulating agents", *J. Neurol. Sci.*, 256:(1):S23-S28 (2007).

Kappos et al., "Effect of early versus delayed interferon beta-1b treatment on disability after a first clinical event suggestive of multiple sclerosis: a 3-year follow-up analysis of the BENEFIT study", *Lancet*, 370(9585):389-397 (2007).

Kuhle et al., "Lack of Association between Antimyelin Antibodies and Progression to Multiple Sclerosis", *N. Engl. J. Med.*, 356(4):371-378 (2007).

Leary et al., "Primary Progressive Multiple Sclerosis Current and Future Treatment Options", *CNS Drugs*, 19(5):369-376 (2005).

Lolli et al., "An N-glucosylated peptide detecting disease-specific autoantibodies, biomarkers of multiple sclerosis", *Proc. Natl. Acad. Sci. U.S.A.*, 102(29):10273-10278 (2005).

Lolli et al., "The glycopeptides CSF114(Glc) detects serum antibodies in multiple sclerosis", *J. Neuroimmunol.*, 167:131-137 (2005).

Mandrioli et al., "A multifactorial prognostic index in multiple sclerosis. Cerebrospinal fluid IgM oligoclonal bands and clinical features to predict the evolution of the disease", *J. Neurol.*, 255:1023-1031 (2008).

Miller et al., "Differential diagnosis of suspected multiple sclerosis: a consensus approach", *Multiple Sclerosis*, 14:1157-1174 (2008).

Miller, D. H., "Biomarkers and Surrogate Outcomes in Neurodegenerative Disease: Lessons from Multiple Sclerosis", *NeuroRx*, 1:284-294 (2004).

Munari et al., "Therapy with glatiramer acetate for multiple sclerosis (Review)", *Cochrane Database of Systematic Rev.*, John Wiley & Sons, 4:CD004678 (2003).

Murray, T.J., "The cardiac effects of mitoxantrone: do the benefits in multiple sclerosis outweigh the risks?", *Exp. Opin. Drug Safety*, 5(2):265-274 (2006).

Perrin et al., "A National Survey of Physician Perspectives of the Unmet Needs in the Treatment of Multiple Sclerosis", *JMCP*, 15(7):572-573 (2009) (Abstract Only).

Pirko et al., "A human antibody that promotes remyelination enters the CNS and decreases lesion load as detected by T2-weighted spinal cord MRI in a virus-induced murine model of MS", *FASEB J.*, 18:1577-1579 (2004).

Pittock et al., "Clinical Implications of Benign Multiple Sclerosis: A 20-Year Population-Based Follow-up Study", *Ann. Neurol.*, 56:303-306 (2004).

Polman et al., "Diagnostic Criteria for Multiple Sclerosis: 2005 Revisions to the 'McDonald Criteria'", *Ann. Neurol.*, 58:840-846 (2005).

Rice et al., "Interferon in relapsing-remitting multiple sclerosis (Review)", *Cochrane Database of Systematic Rev.*, John Wiley & Sons, 4:CD002002 (2001).

Rio et al., "Relationship between MRI lesion activity and response to IFN-$\beta$ in relapsing-remitting multiple sclerosis patients", *Mult. Scler.*, 14:479-484 (2008).

Ritchie et al., "Reference Distributions for Immunoglobulins A, G, and M: A Practical, Simple, and Clinically Relevant Approach in a Large Cohort", *J. Clin. Lab. Anal.*, 12:363-370 (1998).

Rudick et al., "Current approaches to the identification and management of breakthrough disease in patients with multiple sclerosis", *Lancet Neurol.*, 8:545-559 (2009).

Ruggieri et al., "Glatiramer Acetate in Multiple Sclerosis: A Review", *CNS Drug Rev.*, 13(2):178-191 (2007).

Simone et al., "Course and prognosis in early-onset MS. Comparison with adult-onset forms", *Neurol.*, 59(12):1922-1928 (2002).

Sormani et al., "Modelling MRI enhancing lesion counts in multiple sclerosis using a negative binomial model: implications for clinical trials", *J. Neurol. Sci.*, 163(1):74-80 (1999).

Steinman, L., "Multiple sclerosis: a two-stage disease", *Nature Immunol.*, 2(9):762-764 (2001).

Tintore et al., "Baseline MRI predicts future attacks and disability in clinically isolated syndromes", *Neurol.*, 67:968-972 (2006).

Uttner et al., "Reversible impaired memory induced by pulsed methylprednisolone in patients with MS", *Neurol.*, 64(11):1971-1973 (2005).

van Horssen et al., "Extensive extracellular matrix depositions in active multiple sclerosis lesions", *Neurobiol. Dis.*, 24:484-491 (2006).

Vollmer, T., "The natural history of relapses in multiple sclerosis", *J. Neurol. Sci.*, 256(Suppl. 1):S5-S13 (2007).

Warrington et al., "A Recombinant Human IgM Promotes Myelin Repair After a Single, Very Low Dose", *J. Neurosci. Res.*, 85:967-976 (2007).

Yarden and Dotan, "Anti-Collagen IV IgM and anti-Glc(a1,2)Gal(b) (GAAB) IgM can be used for differentiation between Relapsing Remitting Multiple sclerosis (RRMS) patients and patients having other neurological diseases (OND)", Jul. 1, 2009.

Figure 2 – Study design : sequence of events for a patient
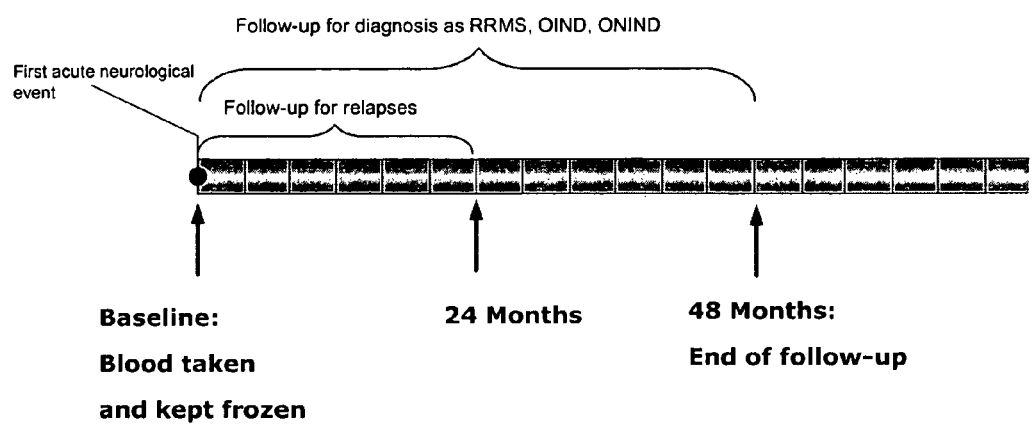

Figure 3 –levels of A) Anti-GAGA6, B) anti-GAGA4, and C) anti-GNa IgM in patients who become RRMS and patients who become OIND and ONIND.
A
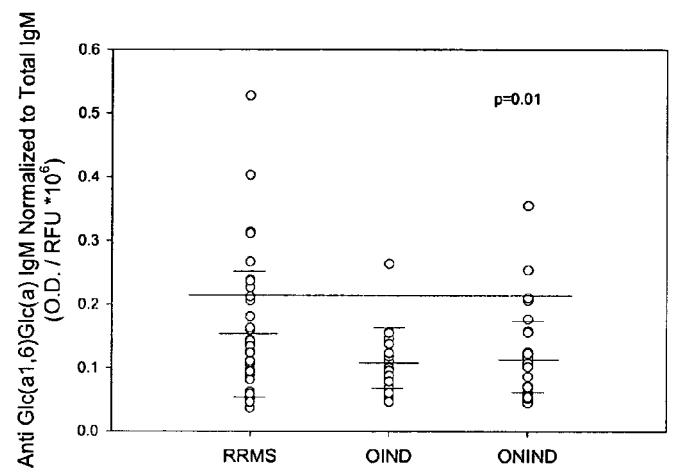
B
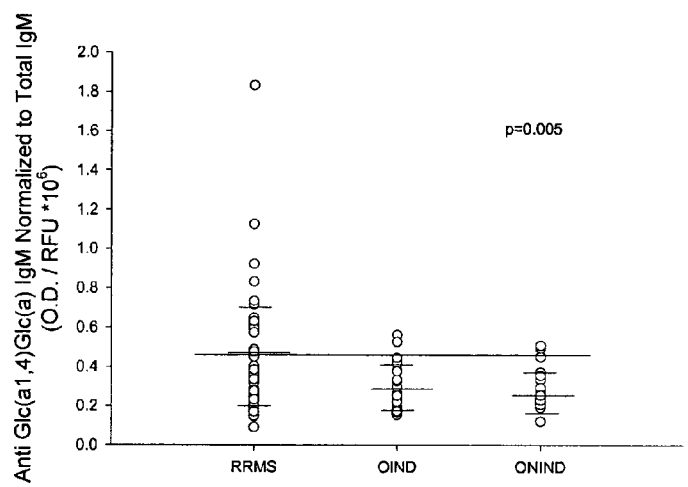

Figure 3-C
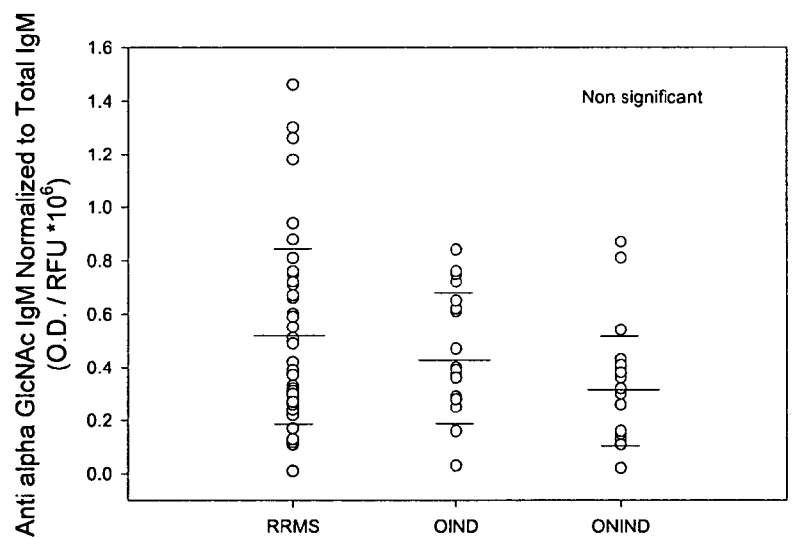

Figure 4 – Comparison between anti-GAGA4 and anti-GAGA6 levels in patients who become RRMS and patients who become OND. Bar represent cut of values.
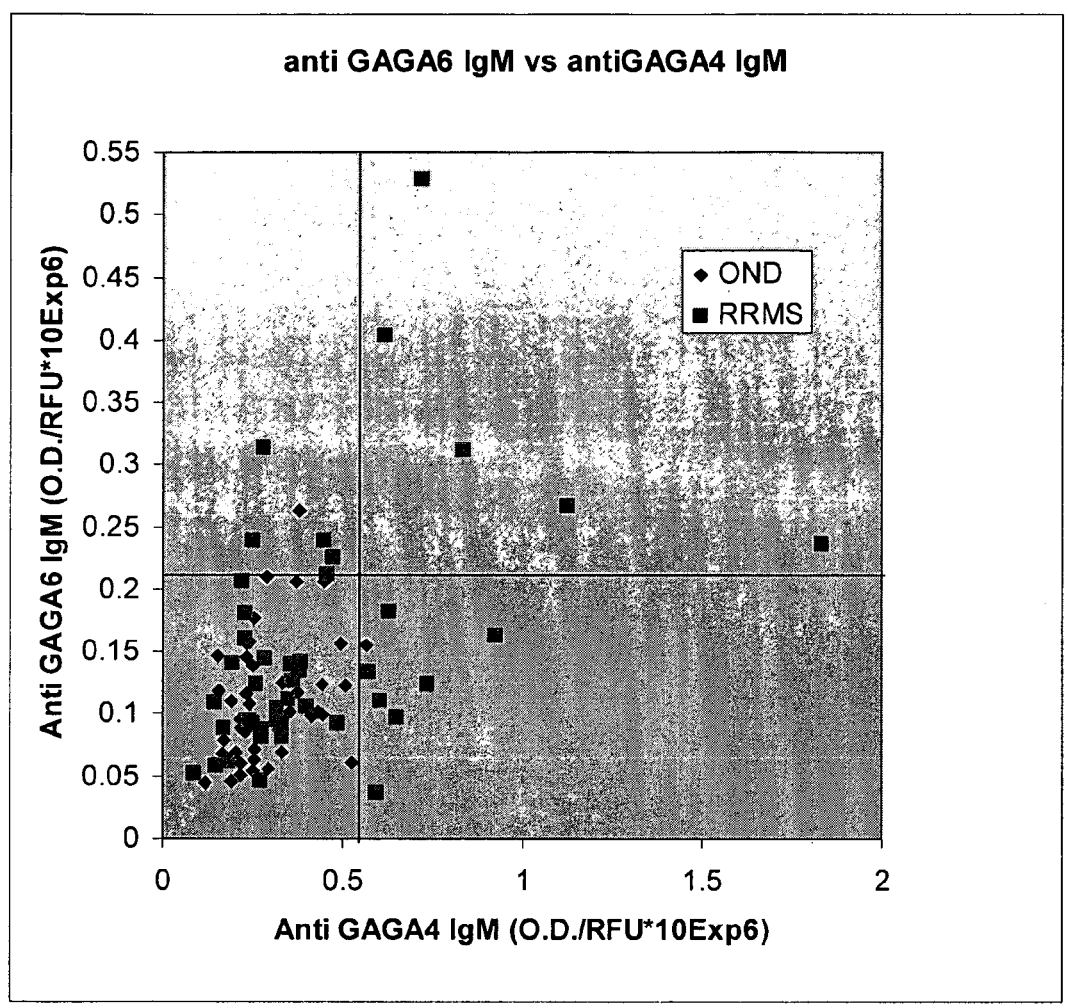

Figure 5 – ROC curves for differentiation according to A) anti-GAGA4, and B) anti-GNa, between patients who become RRMS and had a second relapse with in 2 years and patients who become RRMS but did not had a second attack within 2 years.
A
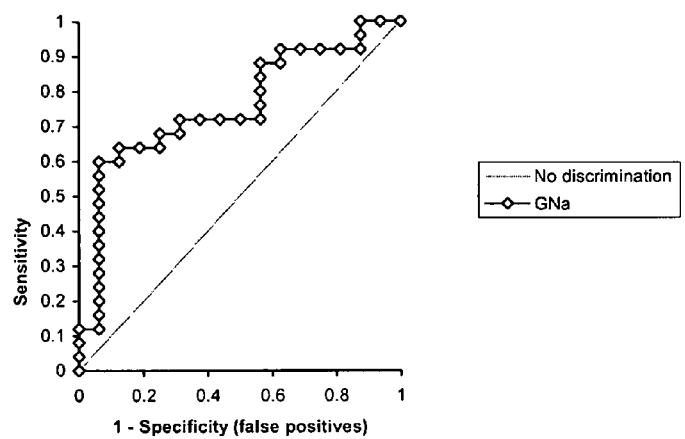
B
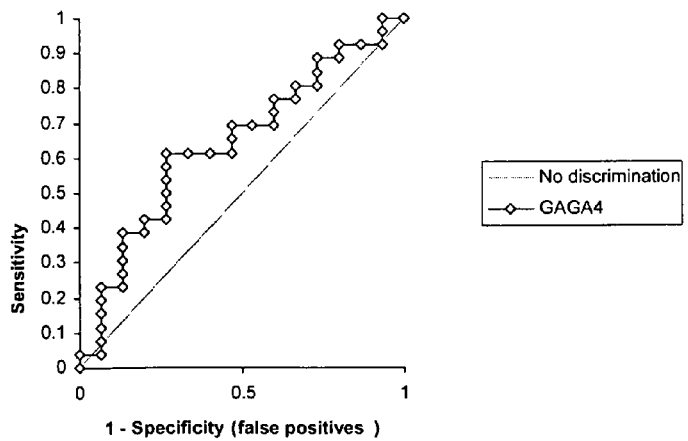

US 7,906,291 B2

METHOD FOR DIAGNOSING MULTIPLE SCLEROSIS

RELATED APPLICATIONS

This application claims priority to, and the benefit of, U.S. Ser. No. 11/047,124, filed Jan. 31, 2005. The contents of this application are incorporated by reference herein in their entirety.

FIELD OF THE INVENTION

The invention relates generally to a method and reagents for diagnosing, and assessing the prognosis of, multiple sclerosis and more particularly to a method and reagents for diagnosing, and assessing the prognosis of, multiple sclerosis by measuring levels of antibodies to glycans in a biological sample.

BACKGROUND OF THE INVENTION

Multiple sclerosis (MS) is a chronic autoimmune inflammatory disease of the central nervous system. It is a common cause of persistent disability in young adults. In patients suffering from MS, the immune system destroys the myelin sheet of axons in the brain and the spinal chord, causing a variety of neurological pathologies. In the most common form of MS, Relapsing-Remitting (RRMS), episodes of acute worsening of neurological function (exacerbations, attacks) are followed by partial or complete recovery periods (remissions) that are free of disease progression (stable).

In order to diagnose a patient with MS two separate events must be recorded. It has been reported that the majority of patients with MS initially present with a clinically isolated syndrome because of an inflammatory demyelinating lesion in the optic nerve, brain stem, or spinal cord. About 50 percent of those patients with a clinically isolated syndrome progress to clinically definite MS (CDMS) within 37 months of presentation. About 40-50% to progress to clinically definite MS within 18 months when assessment is made using magnetic resonance imaging (MRI). The subsequent progression of the disease can vary significantly from patient to patient. The progression can range from a benign course to a classic relapsing-remitting, chronic progressive, or rare fulminant course.

A method for diagnosing MS that facilitates early MS diagnosis and prediction of disease progression or level of activity (Benign, Moderate and Malignant) would be valuable for both managing the disease and providing counsel to the patient. For example, patients diagnosed early with an active MS course could be offered treatments that are beneficial for early MS. In addition, patients at risk for progressing faster and suffering from an additional clinical event in near future would benefit from a more aggressive treatment that will help to postpone these potential next events.

Current methods for assessment and tracking progress of MS are based on assessment and scoring of patients' function in attacks and accumulated disabilities during the attacks. One assessment used to assess MS is the Expanded Disability Status Scale (EDSS). However, the EDSS scoring system does not predict the progression of the disease. In addition, EDSS scoring can be variable because it is based on a subjective assessment of patient function. Methods for diagnosis can also include tracking brain lesions by MRI or testing Cerebrospinal Fluid (CSF) for Oligo-Clonal Banding (OCB). MRI is a physical method for assessment of brain lesions and is used widely for MS diagnosis. However, it typically offers only a very long term predictive value, and the correlation between MRI results and disease activity can be poor. Thus, MRI, OCB or any other existing test cannot be used for short term projections of disease progression, level of activity, or disease management.

Cerebrospinal puncture is an unpleasant invasive procedure that is not suitable for routine use or prognosis. In addition, both methods assess damage only after it has occurred; neither method can predict the onset of attacks or silent, sub-clinical lesions. A further disadvantage in the above-mentioned methods as a way to diagnose MS is that a negative OCB or MRI will not preclude the existence of MS.

Most patients with MS initially present with a clinically isolated syndrome (CIS). Despite the fact that MS will develop in up to 80% of these patients, the course of the disease and the time to conversion is unpredictable at its onset. The disease may remain inactive for many years before the appearance of a second clinical relapse or new lesions on an MRI confirm the diagnosis. Because currently available therapy is only partially effective and side effects are common, many neurologists are uncertain whether to treat all such patients with immunomodulators, or to wait until the diagnosis is confirmed by a second clinical event or the appearance of new MRI lesions. In addition, approved aggressive and potent therapy may not be used because of side effects associated with the therapy, the lack of information on the course of the disease and/or the expected disease progression.

There is a need for a simple serological assay that predicts: i) whether patients at First Neurological Event (FNE) or CIS suggestive of MS will develop MS in a certain timeframe: ii) whether a newly diagnosed relapsing remitting MS that will have a more active disease course and therefore may require aggressive treatment: or iii) whether newly diagnosed MS patient will follow a relatively benign course that allows the patient to postpone immunomodulatory therapy until necessary. This assay would be also useful in helping for diagnosing, assessing the progression of, and managing the treatment of MS. There is in addition an unmet need for developing specific serum based biomarkers for the diagnosis and prognosis of Relapsing Remitting MS (RRMS).

SUMMARY OF THE INVENTION

The invention is based in part on the discovery that MS patients have higher serum levels of IgM antibodies that bind the synthesized glycan structures Glc($\alpha$1,2)Glc($\alpha$) or Glc($\alpha$1,3)Glc($\alpha$) or Glc($\alpha$1,6)Glc($\alpha$) as compared to the serum levels of these antibodies in individuals with other neurological diseases (both chronic, inflammatory or non-inflammatory). The levels of IgM-type anti Glc($\alpha$1,2)Glc($\alpha$) or Glc($\alpha$1,3)Glc($\alpha$) or Glc($\alpha$1,6)Glc($\alpha$) antibodies in serum can act as diagnostics for MS disease, and as staging and prognostic biomarkers for the presence, severity, and activity of MS disease. Levels of the antibodies can also be used to select appropriate treatment, and to track the efficacy of treatment.

Measuring the levels of these antibodies in the blood of MS suspected patients facilitates quick and cost effective early diagnosis of MS patients, disease activity prediction and, when indicated, early prescribing of disease modifying drugs. Monitoring the levels of those antibodies in the blood of defined MS patients also allows for quick and cost effective monitoring of the effects of prescribed drugs and early detection of attacks or sub-clinical silent lesions, thus providing better treatment.

Among the additional advantages of the invention are that the existence of MS in patients can be determined at an earlier stage of the disease, when its symptoms may resemble many other MS-like diseases or when the symptoms are still not sufficient to make a definitive diagnosis of MS. Early diagnosis allows physicians to treat MS earlier in the course of the disease, thereby minimizing or preventing the damage caused by the destruction of myelin and disabilities brought about by this destruction. In addition, the methods disclosed herein enable physicians to follow MS patients regularly in order to assess the disease activity, to monitor therapy, and change treatment once signs for coming attacks appear. For example, an increase in biomarkers indicative of an MS attack may warrant administering methylpredisone, a general anti inflammatory agent commonly administered during attacks, to the patient.

In one aspect, the invention features a method of diagnosing, or assessing the prognosis of, multiple sclerosis in a subject. The method includes providing a test sample from a subject and detecting in the test sample at least one biomarker that is an antibody that binds specifically to a glycan structure. The antibody can be, e.g., anti-Glc($\alpha$1,2)Glc($\alpha$) antibody, an anti-Glc($\alpha$1,3)Glc($\alpha$) antibody, and/or or anti-Glc($\alpha$1,6)Glc ($\alpha$) antibody. The levels of antibody or antibodies in the test sample are compared to a control sample, which is derived from one or more individuals who have multiple sclerosis symptoms and have a known multiple sclerosis status, or from an individual or individuals who do not show multiple sclerosis symptoms. MS status can include, e.g., exacerbations, attacks, remissions, benign, moderate, malignant and stable stages of the disease.

In various embodiments, at least 1, 2 or 3 of these antibodies are detected.

In some embodiments, the method further comprises detecting one or more additional antibodies. The antibody can be, e.g., an anti $\alpha$-Glc antibody (including an anti ($\alpha$-Glc IgM antibody), an anti-Glc($\alpha$1,4)Glc($\alpha$) antibody (including an anti-Glc($\alpha$1,4)Glc($\alpha$) IgM antibody), an anti $\alpha$-GlcNAc antibody (including an anti $\alpha$-GlcNAc IgM antibody), an anti $\beta$-GlcNAc antibody, an anti-Glc($\alpha$1,4)Glc($\beta$) antibody, an anti $\beta$-Glc antibody, an anti $\beta$-Gal antibody, an anti-Glc($\beta$1, 4)Glc($\beta$1,4)Glc($\beta$) antibody, an anti-GlcNAc($\beta$,1,4)GlcNAc ($\beta$) antibody, an anti $\alpha$-L-Araf antibody, an anti $\alpha$-L-Rha antibody, an anti-Gal ($\beta$1,3)[GlcNAc($\beta$1,6)]GalNAc($\alpha$) antibody, an anti-Gal($\beta$1,4)GlcNAc($\alpha$) antibody, an anti-Gal($\beta$1, 3)GalNAc($\alpha$), an anti-Gal($\beta$1,3)GlcNAc($\beta$), an anti $\beta$-GlcA antibody and/or an anti $\alpha$-Xyl antibody. In various embodiments, at least 2, 3, 4, 5, 6, 7, 8, 9, 10, 11, 12, 13, 14, 15, 16, 17 or 18 of these additional antibodies are detected.

In some embodiments, the control sample consists essentially of a population of one or more individuals that do not show symptoms of a multiple sclerosis and do not have multiple sclerosis. In other embodiments, the control sample consists essentially of a population who do show symptoms of a multiple sclerosis and do have multiple sclerosis. In other embodiments, the control sample consists essentially of a population of one or more individuals with neurological diseases other then multiple sclerosis. In other embodiments, the control sample consists essentially of a population of one or more individuals with autoimmune diseases other then multiple sclerosis.

The presence of MS in the control sample can be determined using techniques known in the art, e.g., clinical neurological examination, or an Expanded Disability Status Scale (EDSS) assessment, MRI assessment, or testing for OCB in the CSF or combination of some or all of the techniques.

The test sample can be, e.g., a biological fluid. Examples of biological fluids include, e.g., whole blood, serum, plasma, spinal cord fluid, urine, tears or saliva.

The subject can be either a female or a male.

The antibody detected can be, e.g., an IgM type or an IgA type or an IgG antibody.

In some embodiments, the type of multiple sclerosis detected is early multiple sclerosis.

Also provided by the invention is a method of diagnosing a multiple sclerosis exacerbation in a subject. The method includes providing a test sample from a subject and detecting an anti-Glc($\alpha$1,2)Glc($\alpha$) antibody, an anti-Glc($\alpha$1,3)Glc($\alpha$) antibody and/or an anti-Glc($\alpha$1,6)Glc($\alpha$) antibody in the test sample. The levels of the antibody in the test sample are compared to a control sample, which is derived from one or more individuals whose multiple sclerosis status is known.

In some embodiments, the control sample consists essentially of a population of one or more individuals that do not show symptoms of a multiple sclerosis exacerbation and whose multiple sclerosis status is in remission. A multiple sclerosis exacerbation is diagnosed in the subject if more anti-Glc($\alpha$1,2)Glc($\alpha$) antibody, anti-Glc($\alpha$1.3)Glc($\alpha$) antibody and/or anti-Glc($\alpha$1,6)Glc($\alpha$) antibody is present in the test sample than in the control sample. In other embodiments, the control sample consists essentially of a population of one or more individuals that show symptoms of a multiple sclerosis exacerbation, and a multiple sclerosis exacerbation is diagnosed in the subject if levels of anti-Glc($\alpha$1,2)Glc($\alpha$) antibody, anti-Glc($\alpha$1,3)Glc($\alpha$) antibody and/or anti-Glc($\alpha$1, 6)Glc($\alpha$) antibody are present in similar amounts in the test sample and the control sample.

The test sample can be, e.g., a biological fluid. Examples of biological fluids include, e.g., whole blood, serum, plasma, spinal cord fluid, urine, tears or saliva.

The subject can be either a female or a male.

The antibody detected can be, e.g., an IgM type, an IgA or an IgG type antibody.

In some embodiments, the diagnosis is an early diagnosis of multiple sclerosis exacerbation.

In some embodiments, the subject has been treated with an MS therapeutic agent, e.g., interferon beta or glitamerer acetate administered subcutaneously.

Also within the invention is method for assessing multiple sclerosis disease activity in a subject. The method includes providing a test sample from a subject and determining whether the test sample contains an anti-Glc($\alpha$1,2)Glc($\alpha$) antibody, an anti-Glc($\alpha$1,3)Glc($\alpha$) antibody, and/or anti-Glc ($\alpha$1,6)Glc($\alpha$) antibody. The amount of antibody in the test sample is compared to the amount of the antibody in the control sample, which is derived from one or more individuals whose multiple sclerosis disease activity is known.

In some embodiments, the control sample consists essentially of a population of one or more individuals whose multiple sclerosis disease activity is defined by Expanded Disability Status Scale (EDSS), changes in an EDSS score, frequency of relapses or an MRI assessment.

The test sample can be, e.g., a biological fluid. Examples of biological fluids include, e.g., whole blood, serum, plasma, spinal cord fluid, urine, tears or saliva. If desired, the method may further include selecting a therapeutic agent for treating multiple sclerosis by selecting a therapeutic agent and dosage regimen based on the relative levels of the antibody or antibodies in the test sample and the control sample.

In some embodiments, higher levels of antibodies in the test sample relative to the control sample indicate selection of a therapeutic agent and dosage regimen that is subcutaneous administration of interferon beta (BETAFERON®, AVONEX®, REBIF®), subcutaneous administration of glitamerer acetate (COPAXONE®) or natalizumab (TYSABRI®).

The subject can be either a female or a male.

In a further aspect, the invention provides a method of selecting a therapeutic agent for treating multiple sclerosis. The method includes providing a test sample from a subject diagnosed with, or at risk for, multiple sclerosis and determining whether the test sample contains an anti-Glc(α1,2)Glc(α) antibody, an anti-Glc(α1,3)Glc(α) antibody, or an anti-Glc(α1,6)Glc(α) antibody. Levels of the antibody in the test sample to are compared to levels of antibody in a control sample consisting essentially of one or more individuals whose multiple sclerosis disease activity is known. A therapeutic agent and dosage regimen is selected based on the relative levels of the antibody in the subject sample and the control sample.

In some embodiments, the method further includes determining whether the test sample contains an anti-Glc(α1,2)Glc(α) antibody, an anti-Glc(α1,3)Glc(α) antibody and/or an anti-Glc(α1,6)Glc(α) antibody and comparing the levels of the anti-Glc(α1,2)Glc(α) antibody, anti-Glc(α1,3)Glc(α) antibody and/or anti-Glc(α1,6)Glc(α) antibody in the test sample to levels of antibody in a control sample consisting essentially of one or more individuals whose multiple sclerosis disease severity is known.

In some embodiments, the control sample consists essentially of one or more individuals whose status is no multiple sclerosis or stable multiple sclerosis.

In a further aspect, the invention provides a method to predict whether patients with a CIS suggestive of MS or newly diagnosed relapsing remitting MS will have a highly active disease course and therefore require aggressive treatment, or whether they will follow a more benign course that enables such patients to postpone immunomodulatory therapy until necessary.

The method includes providing a test sample from a subject diagnosed with, or at risk for, multiple sclerosis and determining whether the test sample contains anti-Glc(α1,2)Glc(α) antibody, anti-Glc(α1,3)Glc(α) antibody, and/or anti-Glc(α1,6)Glc(α) antibody. Levels of the antibody in the test sample are compared to levels of antibody in a control sample consisting essentially of one or more individuals whose multiple sclerosis disease activity and course is known. A therapeutic agent and dosage regimen is selected based on the relative levels of the antibody in the subject sample and the control sample.

Also provided by the invention is a kit for diagnosing and predicting disease activity associated with multiple sclerosis. The kit includes a first reagent that specifically detects anti-Glc(α1,2)Glc(α) antibody, an anti-Glc(α1,3)Glc(α) antibody, and/or an anti-Glc(α1,6)Glc(α) antibody, and a second reagent that specifically detects specifically detects a second antibody selected from the group consisting of an anti α-Glc antibody (including an anti α-Glc IgM antibody), an anti-Glc(α1,4)Glc(α) antibody (including an anti-Glc(α1,4)Glc(α) IgM antibody), an anti α-GlcNAc antibody (including an anti α-GlcNAc IgM antibody), an anti β-GlcNAc antibody, an anti-Glc(α1,4)Glc(β) antibody an anti β-Glc antibody, an anti β-Gal antibody, an anti-Glc(β1,4)Glc(β1,4)Glc(β) antibody, an anti-GlcNAc(β,1,4)GlcNAc(β) antibody, an anti α-L-Araf antibody, an anti α-L-Rha antibody, an anti-Gal (β1,3)[GlcNAc(β1,6)]GalNAc(α) antibody, an anti-Gal(β1,4)GlcNAc(α) antibody, an anti-Gal(β1,3)GalNAc(α), an anti-Gal(β1,3)GlcNAc(β), an anti β-GlcA antibody and an anti α-Xyl antibody. The kit may include one or all reagents, and directions for using the kit. The kit optionally includes a reagent that specifically detects an IgM type antibody.

Also within the invention are substrates that include reagents that specifically detect the antibodies disclosed herein, e.g., anti-Glc(α1,2)Glc(α) antibody, an anti-Glc(α1,3)Glc(α) antibody, or an anti-Glc(α1,6)Glc(α) antibody. The invention also includes reagents that specifically detect antibodies used in combination with the antibodies disclosed above, e.g., an anti α-Glc antibody (including an anti α-Glc IgM antibody), an anti-Glc(α1,4)Glc(α) antibody (including an anti-Glc(α1,4)Glc(α) IgM antibody), an anti α-GlcNAc antibody (including an anti α-GlcNAc IgM antibody), an anti β-GlcNAc antibody, an anti-Glc(α1,4)Glc(β) antibody an anti β-Glc antibody, an anti β-Gal antibody, an anti-Glc(β1,4)Glc(β1,4)Glc(β) antibody, an anti-GlcNAc(β,1,4)GlcNAc(β) antibody, an anti α-L-Araf antibody, an anti α-L-Rha antibody, an anti-Gal (β1,3)[GlcNAc(β1,6)]GalNAc(α) antibody, an anti-Gal(β1,4)GlcNAc(α) antibody, an anti-Gal(β1,3)GalNAc(α), an anti-Gal(β1,3)GlcNAc(β), an anti β-GlcA antibody or an anti α-Xyl antibody. The substrate can be, e.g., planar. In a further aspect, the reagents may be connected to a substrate via a linker.

Also within the invention are reagents for diagnosing and predicting disease activity associated with multiple sclerosis, that specifically detects one or more of an anti-Glc(α1,2)Glc(α) antibody, an anti-Glc(α1,3)Glc(α) antibody or an anti-Glc(α1,6)Glc(α) antibody In a further aspect, the reagents may be connected to a substrate via a linker. The substrate may be a bead particles or a planer substrate.

In some embodiments, the reagents that are used to specifically bind and detect those anti glycans antibodies are the specific glycan structures. In other embodiments, the reagents are other molecules that include the specific glycan structures. The glycan or sugar structures can be only the a carbohydrate moeity (including monosaccharides an oligosaccharide or a polysaccharide) or displaying on any solid phase or other macromolecule or any other molecular structure that includes the glycan. The glycan-containing structure can be naturally occurring, e.g., extracted from an organism, or synthetic.

For example, the anti-Glc(α1,2)Glc(α) antibody can be detected using a polymer of these sugar units connected with one or more Glc(α1,2)Glc(α) glycosidic bonds. In another example, the anti-Glc(α1,6)Glc(α) or anti-Glc(α1,3)Glc(α) antibody is detected using the polysaccharide Dextran as an antigen. Dextran is a polymer of sugar units connected with one or more Glc(α1,6)Glc(α) glycosidic bonds with some Glc(α1,3)Glc(α) branches. In a further example, an anti-Glc(α1,4)Glc(α) antibody is detected using the lipo-polysaccharide of *Salmonella typhimurium* that containing Glc(α1,4)Glc(α) structural element In some embodiments, the reagents that are used to specifically bind and detect the anti glycans antibodies of the invention are peptides that mimic the carbohydrate antigens of the invention. The peptides can be used to identify specific anti glycan antibodies.

In some embodiment peptides that mimics the specific carbohydrates of this invention can be used for identification of the specific anti glycan antibodies.

In a further aspect, the invention provides a method of identifying a subject with a first Neurological Event (FNE) who is likely to progress to relapse remitting multiple sclerosis (RRMS). The method includes providing a test sample from a subject with a FNE and detecting in the test sample one or more of an anti-Glc(α1,4)Glc(α) (GAGA4) antibody, and an anti-Glc(α1,6)Glc(α) (GAGA6) antibody. The levels of the levels of the antibody or antibodies in the test sample are compared to a control sample whose RRMS status is known, thereby identifying a FNE subject likely to progress to RRMS.

In some embodiments, the subject with a FNE has symptoms of a Clinically Isolated Syndrome (CIS).

In some embodiments, the method comprises detecting an anti-Glc(α1,4)Glc(α) antibody and an anti-Glc(α1,6)Glc(α) antibody.

In some embodiments, the control sample consists essentially of a population of one or more individuals that do not show RMSS, and the subject is identified as likely to progress to RRMS if the at least one antibody is present at higher levels in the test sample than in the control sample.

In some embodiments, the control sample includes subjects with an Other Neurological Disease (OND).

In some embodiments, the test sample is a biological fluid. The biological fluid can be, e.g., whole blood, serum, plasma, spinal cord fluid, urine, tears or saliva.

In some embodiments, the subject is a female. In other embodiments, the subject is a male.

In some embodiments, at least one of the antibodies is an IgM type antibody. For example, in some embodiments, the Glc(α1,4)Glc(α) antibody and the anti-Glc(α1,6)Glc(α) antibody the antibodies are IgM type antibodies.

In some embodiments, the method further includes calculating an index value for the subject using an algorithm based upon the level of the at least one marker, and identifying a FNE subject likely to progress to RRMS based upon the index value.

In some embodiments, the antibody is detected using a glycan containing a Glc(α1,4)Glc(α) (GAGA4) or Glc(α1,6)Glc(α) (GAGA6) linkage.

In some embodiments, the antibody is detected using an oligosaccharide that includes a glycan containing a Glc(α1,4)Glc(α) (GAGA4) or Glc(α1,6)Glc(α) (GAGA6) linkage.

In some embodiments, the antibody is detected using polymer that includes a glycan containing a Glc(α1,4)Glc(α) (GAGA4) or Glc(α1,6)Glc(α) (GAGA6) linkage. The polymer can be, e.g., a polysaccharide, and can be a naturally occurring polymer or a synthetic polymer.

In a preferred embodiment, the invention features a method of identifying a subject with a First Neurological Event (FNE) who is likely to progress to relapse remitting multiple sclerosis (RRMS). The method includes providing a serum sample from a subject with a FNE, detecting in the test sample at an anti-Glc(α1,4)Glc(α) (GAGA4) IgM antibody, and an anti-Glc(α1,6)Glc(α) (GAGA6) IgM antibody, and comparing the levels of the antibodies in the test sample to a control sample known not to have RRMS. Elevated level of the antibodies in the test sample as compared to the control sample indicates the FNE subject is likely to progress to RRMS.

In a further aspect, the invention provides a method of identifying a subject with RRMS who has active multiple sclerosis disease. The method includes providing a test sample from a subject with RRMS and detecting in the test sample at least one or both of an anti-Glc(α1,4)Glc(α) antibody and an anti-α-GlcNAc (GNa) antibody. The level or levels of the antibody in the test sample to a control sample whose relapsing status is known, thereby identifying an RRMS subject likely to have active multiple sclerosis disease.

In some embodiments, the method comprises detecting an anti-Glc(α1,4)Glc(α) antibody and an anti-α-GlcNAc (GNa) antibody in the test sample.

In some embodiments, a subject identified as having active multiple sclerosis means the subject is assessed as likely to have a subsequent MS attack within two years of obtaining the test sample from the subject, and a therapeutic program is selected based on the assessment.

In some embodiments, the control sample consists essentially of a population of one or more individuals with that do not have active multiple sclerosis disease, and the subject is identified as active multiple sclerosis disease if the at least one antibody is present at higher levels in the test sample than in the control sample.

In some embodiments, the test sample is a biological fluid. The biological fluid can be, e.g., whole blood, serum, plasma, spinal cord fluid, urine, tears or saliva.

In some embodiments, the subject is a female. In other embodiments, the subject is a male.

In some embodiments, the method further includes calculating an index value for the subject using an algorithm based upon the level of the at least one marker, and identifying a FNE subject likely to progress to RRMS based upon the index value.

In some embodiments, the antibody is detected using a Glc(α1,4)Glc(α) glycan and/or a (α-GlcNAc (GNa) glycan.

In one embodiment, the invention provides a method of identifying a subject with RRMS who has active multiple sclerosis disease. The method provides providing a test sample from a subject with RRMS, detecting in the test sample an anti-Glc(α1,4)Glc(α) IgM antibody and an anti-α-GlcNAc (GNa) IgM antibody, and comparing the levels of the antibodies in the test sample to a control sample obtained from a patient or patients that does not have RRMS. An elevated level of the antibodies in the test sample as compared to the control sample indicates the subject has active multiple sclerosis.

In another aspect, the invention provides a purified composition comprising a glycan-containing molecule that is a Glc(α1,2)Glc(α)-containing glycan, a Glc(α1,3)Glc(α)-containing glycan, a Glc(α1,6)Glc(α)-containing glycan, or a α-GlcNAc)-containing glycan. In some embodiments, one, two, three, or all four of these glycans are provided in a single composition as a plurality of glycans.

In some embodiments, the composition further includes a Glc(α1,4)Glc(α)-containing glycan.

In some embodiments, the glycan-containing molecule is provided on an oligosaccharide that comprises, e.g., of 2-20, 2-18, 3-15, or 5-12 monosaccharides.

In some embodiments, at least one of the glycan-containing molecules are present on a polysaccharide.

In some embodiments, the glycan-containing molecule is immobilized on a solid substrate.

Unless otherwise defined, all technical and scientific terms used herein have the same meaning as commonly understood by a person of ordinary skill in the art to which this invention belongs. Although methods and materials similar or equivalent to those described herein can be used in the practice or testing of the present invention, suitable methods and materials are described below. All publications, patent applications, patent, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 2 is a schematic drawing showing a timeline for a sequence of events associated with initial presentation and diagnosis of Multiple Sclerosis in a subject.

FIGS. 3A-C are drawings showing levels of anti-GAGA6 (FIG. 3A); anti-GAGA4 (FIG. 3B); and anti-GNa IgM in patients who become RRMS and patients who become OIND and ONIND (FIG. 3C).

FIG. 4 is plot showing a comparison between anti-GAGA4 and anti-GAGA6 levels in patients who become RRMS and patients who become OND. The bar represents cut-of values.

FIGS. 5A-B are ROC curves for differentiating according to anti-GAGA4 (FIG. 5A), and anti-GNa between patients who become RRMS and had a second relapse with in 2 years and patients who become RRMS but do not have a second attack within 2 years (FIG. 5B).

DETAILED DESCRIPTION OF THE INVENTION

Figure 1:
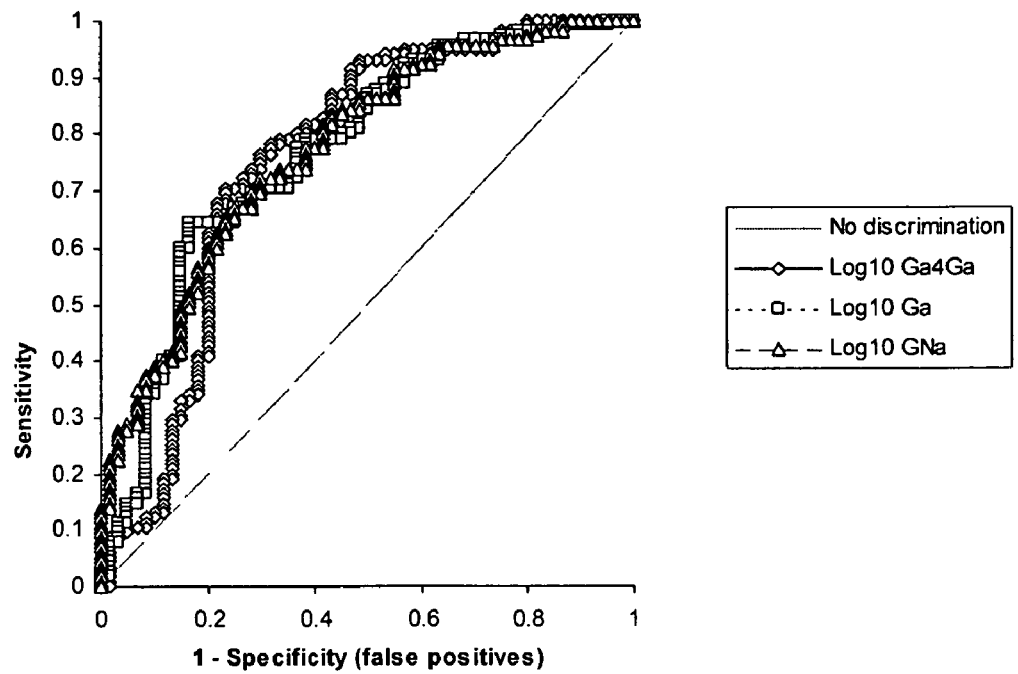
FIG. 1 is a graph showing Receiver Operator Characteristic (ROC) curves for differentiation between MS and OND patients using levels of IgM antibodies against Glc(α1,2)Glc (α)-(Ga2Ga), Glc(α1,3)Glc(α)-Ga3Ga, Glc(α1,6)Glc(α)-Ga6Ga, Glc(α1,4)Glc(α)-Ga4Ga, α-Glc-Ga, and α-GlcNAc-GNa.
Figure 1:
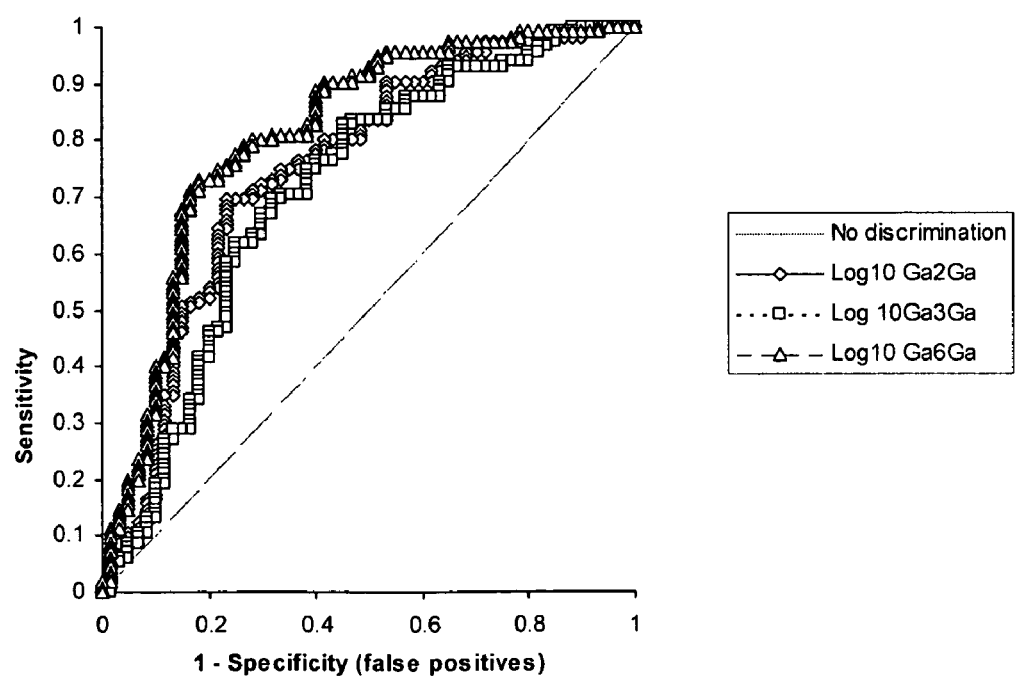

The methods provided herein allow for early diagnosis of initial and recurring multiple sclerosis, as well as prediction of MS disease activity (benign, moderate and malignant), using objectively assessed biomarker levels.

A patient with acute worsening of neurological function has to be diagnosed as a defined MS patient before being eligible for treatment with disease modifying drugs. The physician will have to determine if the patient has MS-like symptoms (such as Younger stroke, Lupus, Vitamin B-12 deficiency, Anti Phospholipid Syndrome, severe migraine) or if they actually have MS. The patient will have to experience a second acute worsening of neurological function (attack) before being diagnosed as a MS patient and be able to start chronic treatment with a MS therapeutic agent such as interferon beta or glatiramer acetate.

Currently, physicians use MRI for the identification of the existence of brain lesions and/or the testing of Cerebrospinal Fluid (CSF) for Oligo Clonal Banding (OCB). If MRI gives a clear result regarding the existence of brain lesions or the presence of OCB in the CSF, the physician may start treatment immediately in order to prevent silent brain lesions. A diagnosis of full MS is currently made only after the second attack or the appearance of a new MRI finding with dissemination in time and space. In case MRI does not give a clear result or there are no OCB in the patients CSF, no MS is diagnosed and treatment is delayed until following a second attack (McDonald et al., Ann Neurol. 50:121-27, 2001).

Most patients with MS initially present with a clinically isolated syndrome (CIS). Despite the fact that MS will develop in up to 80% of these patients, the course of the disease is unpredictable at its onset. The disease may remain inactive for many years before the appearance of a second clinical relapse or new lesions on MRI confirm the diagnosis. Because currently available therapy is only partially effective and side effects are common, many neurologists are uncertain whether to treat all such patients with immunomodulators, or to wait until the diagnosis is confirmed by a second clinical event or the appearance of new MRI lesions. This invention provides a simple serological assay to predict whether patients with a CIS suggestive of MS or newly diagnosed relapsing remitting MS will have a highly active disease course and therefore require aggressive treatment, or whether they will follow a more benign course that enables such patients to postpone immunomodulatory therapy until necessary. This assay is also useful for helping diagnosing MS.

The methods disclosed herein can be performed by extracting blood from a patient with acute worsening of neurological function and suspected to have MS or who is an already defined RRMS patient. The method can identify the existence of MS and to predict the up coming course of the diseases by measuring anti-Glc(α1,2)Glc(α) antibody, anti-Glc(α1,3)Glc(α) antibody, and/or anti-Glc(α1,6)Glc(α) antibody levels. If the level of at least one of these antibodies is significantly higher then the average level of these antibodies in sera of healthy individuals, patients with neurological diseases other then MS, or patients with autoimmune diseases other then MS, the patient is diagnosed as an MS patient without the need to wait for a second attack or for further MRI findings. In addition, the quick diagnosis allows for treatment to begin immediately.

Screening the patient's blood and determining the level of biomarkers disclosed herein, e.g., anti-Glc(α1,2)Glc(α) antibody, anti-Glc(α1,3)Glc(α) antibody or anti-Glc(α1,6)Glc(α) antibody, allows for accurate monitoring of therapy. For example, one first line of treatment for MS is interferon β (e.g., IFNβ-1a and INFβ-1b). The current evaluation of effectiveness and required dosage of the drug is based on continued monitoring of several clinical scores. Currently, the EDSS score and its change over time (e.g., by comparing the difference in the EDSS every 3-6 months) is the main clinical parameter for disease management. An important component of the assessment is the level of fatigue and depression experienced by the patient. The fatigue and or depression can be a symptom of MS, as an autoimmune disease, or a side effect from using IFNβ. Identifying the cause of the fatigue is important for managing the treatment. For example, if the fatigue is a result of a side effect of the interferon, the physician will consider lowering the dosage or even exchanging it for another drug. However, if the fatigue is due to the MS symptoms, the physician will have to consider increasing the drug dosage. Significant decreases in antibody levels indicate that the patient is responding well to the given drug.

Currently there is no way to predict the onset of attacks and sub-clinical silent lesions in MS patients. MRI and clinical evaluation of the patients can only reveal damage that has already occurred. Periodical measurement of the level of a few anti glycan antibodies (for example, anti-Glc(α1,2)Glc(α) antibody, anti-Glc(α1,3)Glc(α) antibody, and/or anti-Glc(α1,6)Glc(α) antibody) in the patient's blood according to the method described herein allows for physicians to predict the upcoming disease activity (e.g. frequency of clinical attacks and appearance of sub clinical MRI silent lesions) based upon an increase in levels of these antibodies.

All the glycan structures that are discussed in this disclosure, unless mentioned otherwise are connected to in the indicated anomericity α or β through linker to solid phase.

In some embodiments peptides that mimic the specific glycans of this invention can be used for identification of the specific anti glycan antibodies. The peptides that mimic carbohydrates can be identified, for example, by screening a filamentous phage-displayed random peptide library (Zhan et al., Biochem Biophys Res Commun. 308:19-22, 2003; Hou et al., J Immunol. 170:4373-79, 2003).

Most patients with MS) initially present with a clinically isolated syndrome (CIS). Despite the fact that clinically definite MS will develop in up to 80% of these patients, the course of the disease is unpredictable at its onset. The disease may remain inactive for many years before the appearance of a second clinical relapse or new lesions on MRI confirm the diagnosis. Because currently available therapy is only partially effective and side effects are common, many neurologists are uncertain whether to treat all such patients with immunomodulators, or to wait until the diagnosis is confirmed by a second clinical event or the appearance of new MRI lesions.

The invention provides a simple serological assay that may be used to predict whether patients with a CIS suggestive of MS or newly diagnosed relapsing remitting MS will have a highly active disease course and therefore require aggressive treatment, or whether they will follow a more benign course that enables such patients to postpone immunomodulatory therapy until necessary.

The invention additionally provides a simple serological test for the definite confirmation of MS and of the level of the risk in individuals presenting a primary acute demyelinating event. Ninety percent of patients with MS initially present with a clinically isolated syndrome due to an inflammatory demyelinating lesion in the optic nerve, brain stem, or spinal cord (O'Riordan et al., Brain 121: 495-503, 1998). Thirty percent of these patients with clinically isolated syndrome will have progression to definite MS within 12 month after presentation (Brex et al., N. Engl. J. Med. 346:158-164, 2002; O'Riordan et al., Brain 121: 495-503, 1998; Jacobs et al., Ann. Neurol. 41:392-98, 1997), but no more than 80% of patients with a clinically primary event will develop clinically definite MS (Weinshenker et al., Brain 112:1419-28, 1989). Thus, it is desirable to unambiguously confirm and stage MS prior to commencing treatment with disease modifying drugs.

The methods can be used to determine whether a particular treatment MS treatment regimen is warranted for a particular patient. Patients at high risk for rapid progression to definite MS can be offered disease-modifying treatments that are beneficial in early multiple sclerosis (Comi et al., Lancet 351:1576-82, 2001; Jacobs et al., N. Engl. J. Med. 343:898-904, 2000). On the other hand, for patients at low risk, and who have a chance of remaining relapse free for several years after an initial demyelinating event, immunomodulatory therapy might be postponed until necessary. Thus, an advantage of the invention is better disease management at the early days of the disease.

The presence of antibodies to Glc($\alpha$1,2)Glc($\alpha$), Glc($\alpha$1,3) Glc($\alpha$) and/or Glc($\alpha$1,6)Glc($\alpha$) can be combined with other diagnostic tests for diagnosing multiple sclerosis. One such test is the MS-associated antibodies disclosed in WO 2004/015420, the contents of which are incorporated by reference in their entirety. These antibodies include, e.g., an anti $\alpha$-Glc antibody (including an anti $\alpha$-Glc IgM antibody), an anti-Glc ($\alpha$1,4)Glc($\alpha$) antibody (including an anti-Glc($\alpha$1,4)Glc($\alpha$) IgM antibody), an anti $\alpha$-GlcNAc antibody (including an anti $\alpha$-GlcNAc IgM antibody), an anti $\beta$-GlcNAc antibody, an anti-Glc($\alpha$1,4)Glc($\beta$) antibody an anti $\beta$-Glc antibody, an anti $\beta$-Gal antibody, an anti-Glc($\beta$1,4)Glc($\beta$1,4)Glc($\beta$) antibody, an anti-GlcNAc($\beta$1,4)GlcNAc($\beta$) antibody, an anti $\alpha$-L-Araf antibody, an anti $\alpha$-L-Rha antibody, an anti-Gal ($\beta$1,3) [GlcNAc($\beta$1,6)]GalNAc($\alpha$) antibody, an anti-Gal($\beta$1,4) GlcNAc($\alpha$) antibody, an anti-Gal($\beta$1,3)GalNAc($\alpha$), an anti-Gal($\beta$1,3)GlcNAc($\beta$), an anti $\beta$-GlcA antibody or an anti $\alpha$-Xyl antibody.

The methods are typically performed using reagents that specifically bind to the anti-glycan antibodies. The reagents can be, e.g., the specific glycan structures. Alternatively, the reagents can be other molecules or macromolecules that include the specific glycan structure.

In some embodiments, the reagents that are used to specifically bind and detect those anti glycans antibodies are the specific glycan structures. In other embodiments, the reagents are other molecules that include the specific glycan structure. The glycan or sugar structures can be only the carbohydrate moiety (including monosaccharides an oligosaccharide or a polysaccharide) or displaying on any solid phase or other macromolecular any other molecular structure that includes the glycan. The glycan-containing structure can be naturally occurring, e.g., extracted from an organism, or synthetic. For example, the Glc($\alpha$1,2)Glc($\alpha$) antibody can be detected using a polysaccharide that includes a polymer with one or more Glc($\alpha$1,2)Glc($\alpha$) linkages.

In another example, the anti-Glc($\alpha$1,6)Glc($\alpha$) or anti-Glc ($\alpha$1,3)Glc($\alpha$) antibody is detected using the polysaccharide dextran as an antigen. Dextran is a polymer of sugar units connected with one or more Glc($\alpha$1,6)Glc($\alpha$) glycosidic bonds with some Glc($\alpha$1,3)Glc($\alpha$) branches. Additionally, an anti-Glc($\alpha$1,4)Glc($\alpha$) antibody is detected using the lipo-polysaccharide of *Salmonella typhimurium* that containing Glc($\alpha$1,4)Glc($\alpha$) structural element (Holme et al., et al., Carbohydr. Res 8:43-55, 1968). See also U.S. Patent Application publication No. 20040241763 (especially FIG. 11B, and Table 5 of the application), which shows that antibodies to Glc(1,4)Glc(a) purified from MS patients sera react with the lipopolysaccharide from lipo-polysaccharide of *Salmonella typhimurium*.

Thus, the glycan itself can be used for detecting the corresponding antibody or antibodies, as can any other molecular structure that includes the glycan.

If desired, peptides that mimic carbohydrate antigens can be used in the methods and compositions described herein. The peptides can be used to identify specific anti glycan antibodies. Peptides which mimic structures recognized by antiglycan antibodies can be identified using methods known in the art, e.g., by screening a filamentous phage-displayed random peptide library (Zhan et al., Biochem Biophys Res Commun. 308:19-22, 2003; Hou et al., J Immunol. 17:4373-79, 2003).

Glycan antigens used to identify various anti-glycan antibodies can be obtained from a variety of other sources so long as the antigen is capable of binding specifically to the given anti-glycan. Binding to anti-glycan antibodies can be performed using variety of other immunoassay formats known in the art, including competitive and non-competitive immunoassay formats can also be used (Self and Cook, Curr. Opin. Biotechnol. 7:60-65 (1996), which is incorporated by reference). Other assays include immunoassays, such as enzyme-linked immunosorbent assays (ELISAs). An enzyme such as horseradish peroxidase (HRP), alkaline phosphatase (AP), $\beta$-galactosidase or urease can be linked to a secondary antibody selective for a primary anti-glycan antibody of interest. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a $\beta$-galactosidase detection system can be used with the chromogenic substrate o-nitrophenyl-a $\beta$-D-galactopyranoside (ONPG), which yields a soluble product detectable at 410 nm, or a urease detection system can be used with a substrate such as urea-bromocresol purple (Sigma Immunochemicals, St. Louis, Mo.). A useful secondary antibody linked to an enzyme can be obtained from a number of commercial sources; goat F(ab')$_2$ anti-human IgG-alkaline phosphatase, for example, can be purchased from Jackson Immuno-Research (West Grove, Pa.).

Immunoassays encompass capillary electrophoresis based immunoassays (CEIA) and can be automated, if desired. Immunoassays also can be used in conjunction with laser induced fluorescence (see, for example, Schmalzing and Nashabeh, Electrophoresis 18:2184-93 (1997)); Bao, J. Chromatogr. B. Biomed. Sci. 699:463-80 (1997), each of which is incorporated herein by reference). Liposome immunoassays, such as flow-injection liposome immunoassays and liposome immunosensors, also can be used (Rongen et al., J. Immunol. Methods 204:105-133 (1997)).

A radioimmunoassay can also be used for determining whether a sample is positive for a glycan antibody, or for determining the level of anti-glycan antibodies in a sample. A radioimmunoassay using, for example, an $^{125}$Iodine-labeled secondary antibody (Harlow and Lane, Antibodies A Laboratory Manual Cold Spring Harbor Laboratory: New York, 1988, which is incorporated herein by reference) is encompassed within the invention.

A secondary antibody may alternatively be labeled with a chemiluminescent marker. Such a chemiluminescent secondary antibody is convenient for sensitive, non-radioactive detection of anti-glycan antibodies and can be obtained commercially from various sources such as Amersham Lifesciences, Inc. (Arlington Heights, Ill.).

A detectable reagent may also be labeled with a fluorochrome. Appropriate fluorochromes include, for example, DAPI, fluorescein, Hoechst. 33258, R-phycocyanin, B-phycoerythrin, R-phycoerythrin, rhodamine, Texas red or lissamine. A particularly useful fluorochrome is fluorescein or rhodamine. Secondary antibodies linked to fluorochromes can be obtained commercially. For example, goat F(ab')$_2$ anti-human IgG-FITC is available from Tago Immunologicals (Burlingame, Calif.).

A signal from the detectable reagent can be analyzed, for example, using a spectrophotometer to detect color from a chromogenic substrate; a radiation counter to detect radiation, such as a gamma counter for detection of $^{125}$Iodine; or a fluorometer to detect fluorescence in the presence of light of a certain wavelength. For detection of enzyme-linked reagents, a quantitative analysis of the amount of anti-glycan antibodies can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

Other methods include, e.g., flow cytometry (including bead based immunoassays), and phage display technology for expressing a recombinant antigen specific for an anti-glycan antibody. Phage particles expressing the antigen specific for a desired anti-glycan antibody can be anchored, if desired, to a multiwell plate using an antibody such as an anti phage monoclonal antibody (Felici et al., "Phage-Displayed Peptides as Tools for Characterization of Human Sera" in Abelson (Ed.), Methods in Enzymol. 267, San Diego: Academic Press, Inc. (1996), which is incorporated by reference herein).

Interpreting Anti-Glycan Antibody Binding Data

Typically, binding of anti-glycan antibodies to glycans in a sample is compared to a reference population, and differences in levels of the anti-glycan antibodies in the two samples are compared. The threshold for determining whether a test sample is scored positive based on its ant-glycan antibody profile can be altered depending on the sensitivity or specificity desired. The clinical parameters of sensitivity, specificity, negative predictive value, positive predictive value and efficiency are calculated using true positives, false positives, false negatives and true negatives. A "true positive" sample is a sample positive for MS according to art-recognized methods for diagnosing MS, RRMS, etc., which is also diagnosed positive according to a method of the invention. A "false positive" sample is a sample negative by an art-recognized method, which is diagnosed positive according to a method of the invention. Similarly, a "false negative" is a sample positive for an art-recognized analysis, which is diagnosed negative according to a method of the invention. A "true negative" is a sample negative for the assessed trait by an art-recognized method, and also negative according to a method of the invention. See, for example, Mousy (Ed.), Intuitive Biostatistics New York: Oxford University Press (1995), which is incorporated herein by reference.

As used herein, the term "sensitivity" means the probability that a laboratory method is positive in the presence of the measured trait. Sensitivity is calculated as the number of true positive results divided by the sum of the true positives and false negatives. Sensitivity essentially is a measure of how well a method correctly identifies those with disease. In a method of the invention, the anti-glycan antibody values can be selected such that the sensitivity of diagnosing an individual is at least about 60%, and can be, for example, at least about 65%, 70%, 75%, 80%, 85%, 90% or 95%.

As used herein, the term "specificity" means the probability that a method is negative in the absence of the measured trait. Specificity is calculated as the number of true negative results divided by the sum of the true negatives and false positives. Specificity essentially is a measure of how well a method excludes those who do not have the measured trait. The anti-glycan cut-off value can be selected such that, when the sensitivity is at least about 70%, the specificity of diagnosing an individual is in the range of 30-60%, for example, 35-60%, 40-60%, 45-60% or 50-60%.

The term "positive predictive value," as used herein, is synonymous with "PPV" and means the probability that an individual diagnosed as having the measured trait actually has the disease. Positive predictive value can be calculated as the number of true positives divided by the sum of the true positives and false positives. Positive predictive value is determined by the characteristics of the diagnostic method as well as the prevalence of the disease in the population analyzed. In a method of the invention, the anti-glycan antibody cut-off values can be selected such that the positive predictive value of the method in a population having a disease prevalence of 15% is at least about 5%, and can be, for example, at least about 8%, 10%, 15%, 20%, 25%, 30% or 40%.

As used herein, the term "efficiency" means the accuracy with which a method diagnoses a disease state. Efficiency is calculated as the sum of the true positives and true negatives divided by the total number of sample results and is affected by the prevalence of the trait in the population analyzed. The anti-glycan antibody cut-off values can be selected such that the efficiency of a method of the invention in a patient population having an MS disease prevalence of 15% is at least about 45%, and can be, for example, at least about 50%, 55% or 60%.

The invention will be illustrated in the following non-limiting examples.

Example 1

Higher Levels of Anti-Glc(α1,2)Glc(α), Glc(α1,3)Glc(α), and Glc(α1,6)Glc(α) IgM Antibodies are Found in Sera of MS Patients vs OND Patients Recruitment of Patients One hundred and fifteen (115) Outpatients aged 18-55 years with clinically definite and laboratory-supported MS, according to the Poser criteria (Poser et al., Ann Neurol 13, 227-231, 1883), were eligible for the study. Inclusion criteria for patients with RRMS were a history of at least two clearly identified and documented relapses in the 2 years prior to study entry, and being ambulant, defined by Kurtzke's expanded disability status scale (EDSS) (Kurtzke, Neurology 33, 1444-1452, 1983) of 0-6.5. Relapse was defined as the appearance or reappearance of one or more neurological abnormalities that persisted for at least 24 h, and which had been preceded by at least 30 days of stable or improved neurological state. Exclusion criteria were corticosteroids treatment in the preceding 3 months, previous immunosuppressive therapy with cytotoxic activity or lymphoid irradiation, as well as pregnancy or lactation. Signed informed consent was obtained from patients, and the study was approved by the Ethical Committee of the Lady Davis, Carmel Medical Center, Israel and by the Ethical Committee of Sourasky Medical Center, Tel Aviv, Israel.

Sera of 60 patients affected by other neurological disease (OND) were obtained from Genomics Collaborative, MA, USA, or obtained under informed consent from patients admitted to the Neuroimmunology Unit, Carmel Medical Center, Israel The blood samples were collected in evacuated silicon-coated tubes containing gel for the separation of sera from the blood clot (Estar Technologies, Israel). After coagulation of the blood, serum was separated by centrifugation, collected and kept frozen at −25° C. until use. The laboratory evaluations were conducted in a blind manner in relation to the clinical findings.

Glycan Array

All serum samples were tested using GlycoChip®. The glycans were covalently bound to the surface through a linker, as previously described (Schwarz et al., Glycobiology 13, 749-754, 2003; Dukler and Dotan, WIPO, Vol. WO2002IL0000101, Glycominds Ltd., 2002). Briefly, an oligomer of 1,8-diamino-3,6-dioxaoctan (Sigma, St. Louis, Mo.) was synthesized and coupled to the solid support. Consequently, pNP-saccharide conjugates were reduced by sodium dithionite to pAP-saccharide derivatives and reacted with cyanochloride (Sigma)-activated linker. The following p-nitrophenyl glycans derivatives were spotted on the slides: Glc(α1,2)Glc(α), Glc(α1,3)Glc(α), Glc(α1,6)Glc(α), Glc(α1,4)Glc(α), α-Glc, and α-GlcNAc. The glycans were printed in 6 sub arrays on each slide, 4 spots for each glycan per sub array.

Fluorescent Assay for Specific Glycan-Binding Antibodies Using Glass Slide GlycoChip®

An adhesive silicon superstructure attached to the slide after the printing enables to apply 6 different serum samples on each slide simultaneously, 4 patient samples and high and low plasma controls.

Serum samples (diluted 1:80 in TBST containing 1% BSA) were incubated for 1 h on the slides. After washing in TNTT buffer (20 mM Tris-HCl pH 7.2, 2 M NaCl, 0.05% Tween-20, 0.05% Triton X-100) labeling reagents were incubated on the glass slides in a Tecan HS-4800 hybridization system. Biotinylated goat anti-human IgM (1:500) and Alexa-488-labeled streptavidin (1:150; Molecular Probes, OR, USA) were incubated sequentially with washings in between for 1 h at 32° C. in the light-protected and temperature-controlled environment of the hybridization system. Slides were scanned using an Axon 4100 array scanner controlled by GenPix (Axon, CA, USA). Images were analyzed using ArrayPro Analyzer 4.5.1.48 (Media Cybernetics, CA, USA).

The level of all anti-glycan IgM antibodies tested was significantly higher in MS patients vs. patients with other neurological diseases. Descriptive statistics for anti-glycan IgM antibody levels in 115 multiple sclerosis patients and 60 patients with other neurological diseases are shown in Table 1. The RFU signals were Log 10 transformed for achieving normal distribution. The Receiver Operator Characteristic (ROC) curve for differentiation between MS and OND patients is shown in FIG. 1. The results show that all the glycans can differentiate between MS patients and OND patients with 90% specificity and 40-60% sensitivity. Using cutoff values for 90% specificity, it was determined for each of the patients whether the patient was positive (above cutoff) or negative (below cutoff) for each of the antigens tested.

TABLE 1

| | Mean Log10(RFU), (SD) | |
|---|---|---|
| Sugar Antigen | MS | OND |
| Glc(α1,2)Glc(α) | 0.51 (0.19) | 0.32 (0.21)* |
| Glc(α1,3)Glc(α) | 0.45 (0.20) | 0.31 (0.23)* |
| Glc(α1,6)Glc(α) | 0.48 (0.21) | 0.20 (0.23)* |
| Glc(α1,4)Glc(α) | 0.52 (0.20) | 0.32 (0.25)* |
| α-Glc | 0.37 (0.18) | 0.17 (0.20)* |
| α-GlcNAc | 0.61 (0.25) | 0.33 (0.24)* |

SD, standard deviation;
MS, multiple sclerosis;
OND, other neurological diseases,
RFU, relative fluorescence units.
*p < 0.000001 versus MS Levels of anti-glycan antibodies Glc(α1,4)Glc(α)-Ga4Ga, α-Glc-Ga, α-GlcNAc-GNa, Glc(α1,2)Glc(α)-Ga2Ga, Glc(α1,3Glc(α)-Ga3Ga, Glc(α1,6)Glc(α)-Ga6Ga were determined for each patient. The results are shown in Table 2. Gray patterned cells in the table represent antibody level above cutoff for 90% specificity. The results show that that there are MS patients who are positive to one or more of Glc(α1,2)Glc(α), Glc(α1,3)Glc(α), or Glc(α1,6)Glc(α) and are not positive for Glc(α1,4)Glc(α), α-Glc, or α-GlcNAc. For example, patient 5138 is positive only for anti Glc(α1,2)Glc(α), patients 5414 and 5415 are positive only for anti Glc(α1,3)Glc(α) and patient 5446 is positive only for anti Glc(α1,6)Glc(α), those patients can be diagnosed only by using only the relevant antigen. Thus, each antigen has a unique specificity contribution for more accurate diagnosis of MS. These results show that anti-Glc(α1,2)Glc(α), Glc(α1,3)Glc(α), and Glc(α1,6)Glc(α) IgM antibodies are found at higher levels in MS patients vs. OND patients. Therefore, these antibodies are useful in the diagnosis of MS patients either by alone or in combination with other antigens.

TABLE 2

| Patient I.D | Disease | Ga4Ga | Ga | GNa | Ga2Ga | Ga3Ga | Ga6Ga |
|---|---|---|---|---|---|---|---|
| 302 | MS | 2.09 | 1.48 | 1.22 | 2.01 | 2.27 | 2.98 |
| 303 | MS | 1.47 | 1.26 | 3.02 | 2.43 | 3.40 | 1.45 |
| 308 | MS | 4.70 | 3.73 | 5.35 | 5.68 | 2.98 | 4.26 |
| 309 | MS | 2.06 | 1.65 | 1.64 | 3.41 | 1.98 | 1.79 |
| 312 | MS | 1.80 | 1.34 | 1.38 | 3.70 | 1.69 | 1.59 |
| 313 | MS | 5.47 | 3.46 | 3.03 | 4.60 | 6.18 | 4.55 |
| 314 | MS | 4.30 | 2.61 | 6.18 | 6.74 | 4.54 | 4.02 |
| 316 | MS | 3.30 | 3.12 | 8.39 | 3.27 | 2.61 | 2.39 |
| 318 | MS | 3.57 | 2.99 | 3.41 | 2.12 | 2.52 | 5.70 |
| 321 | MS | 2.24 | 2.98 | 5.35 | 4.49 | 3.26 | 2.86 |
| 322 | MS | 4.15 | 2.78 | 2.74 | 3.03 | 2.77 | 2.72 |
| 323 | MS | 2.20 | 1.61 | 4.46 | 3.34 | 2.62 | 4.61 |
| 324 | MS | 4.45 | 2.46 | 7.09 | 3.95 | 3.90 | 2.47 |
| 326 | MS | 3.11 | 3.61 | 4.93 | 11.21 | 3.22 | 7.06 |
| 328 | MS | 5.33 | 2.50 | 4.32 | 1.90 | 2.95 | 3.43 |
| 5086 | MS | 2.70 | 1.76 | 6.60 | 3.47 | 3.23 | 3.31 |
| 5089 | MS | 2.70 | 2.48 | 10.78 | 3.58 | 2.59 | 2.70 |
| 5090 | MS | 4.88 | 2.54 | 4.72 | 3.05 | 3.64 | 3.21 |
| 5093 | MS | 3.36 | 3.13 | 4.30 | 6.70 | 2.58 | 3.97 |
| 5098 | MS | 3.15 | 1.46 | 12.01 | 2.55 | 2.50 | 2.21 |
| 5103 | MS | 9.16 | 4.41 | 13.14 | 8.18 | 5.78 | 6.95 |
| 5106 | MS | 11.15 | 3.57 | 11.36 | 4.26 | 7.68 | 4.17 |
| 5110 | MS | 1.93 | 1.39 | 2.13 | 1.98 | 1.78 | 2.52 |
| 5111 | MS | 4.39 | 2.37 | 3.22 | 4.83 | 3.11 | 4.58 |
| 5113 | MS | 1.89 | 1.44 | 2.94 | 3.13 | 1.97 | 1.69 |
| 5119 | MS | 2.37 | 2.12 | 4.09 | 2.27 | 3.04 | 3.06 |
| 5120 | MS | 7.79 | 2.48 | 7.79 | 4.42 | 3.95 | 5.41 |
| 5121 | MS | 4.81 | 1.90 | 9.18 | 3.32 | 3.93 | 4.00 |
| 5126 | MS | 3.77 | 1.97 | 6.20 | 2.12 | 3.72 | 3.93 |
| 5129 | MS | 10.39 | 2.27 | 4.43 | 4.25 | 3.94 | 6.10 |
| 5130 | MS | 2.97 | 2.93 | 3.96 | 1.62 | 1.87 | 1.38 |
| 5137 | MS | 3.23 | 2.44 | 11.75 | 4.35 | 2.30 | 2.62 |
| 5138 | MS | 1.94 | 2.20 | 3.51 | 6.55 | 1.88 | 2.66 |
| 5139 | MS | 2.04 | 1.35 | 3.62 | 1.23 | 2.81 | 1.69 |
| 5145 | MS | 1.35 | 0.76 | 1.24 | 1.34 | 1.27 | 0.90 |
| 5158 | MS | 2.04 | 2.21 | 1.98 | 1.69 | 1.75 | 2.15 |
| 5159 | MS | 4.80 | 2.96 | 2.96 | 2.96 | 2.77 | 3.66 |
| 5163 | MS | 4.17 | 3.24 | 5.20 | 3.73 | 2.71 | 4.95 |
| 5174 | MS | 3.83 | 2.66 | 3.99 | 3.18 | 2.25 | 3.65 |
| 5175 | MS | 1.35 | 1.19 | 2.11 | 1.73 | 1.62 | 1.03 |
| 5176 | MS | 3.41 | 2.80 | 5.15 | 2.69 | 2.07 | 2.78 |
| 5177 | MS | 6.25 | 2.58 | 3.42 | 4.42 | 8.39 | 2.91 |
| 5204 | MS | 2.59 | 1.29 | 2.07 | 2.01 | 1.32 | 2.22 |
| 5207 | MS | 4.49 | 2.49 | 2.81 | 2.17 | 2.40 | 2.84 |
| 5208 | MS | 4.97 | 4.68 | 7.54 | 3.06 | 2.48 | 3.84 |
| 5211 | MS | 4.58 | 1.43 | 3.81 | 2.78 | 1.99 | 1.25 |
| 5212 | MS | 2.02 | 1.70 | 4.15 | 2.54 | 2.23 | 2.42 |
| 5213 | MS | 2.30 | 2.41 | 3.72 | 2.05 | 2.29 | 3.02 |
| 5214 | MS | 3.39 | 2.70 | 6.21 | 3.23 | 2.64 | 3.12 |
| 5215 | MS | 4.01 | 3.01 | 3.99 | 3.02 | 2.43 | 4.38 |
| 5216 | MS | 9.81 | 2.35 | 2.43 | 3.12 | 2.94 | 3.75 |
| 5217 | MS | 3.91 | 3.00 | 6.34 | 3.11 | 2.15 | 3.01 |
| 5219 | MS | 2.04 | 2.76 | 2.35 | 4.28 | 1.42 | 1.60 |
| 5230 | MS | 5.49 | 4.02 | 4.30 | 5.11 | 3.19 | 4.20 |
| 5231 | MS | 2.74 | 1.98 | 4.12 | 5.17 | 3.69 | 2.94 |
| 5232 | MS | 4.81 | 3.77 | 12.05 | 4.40 | 11.63 | 7.42 |
| 5240 | MS | 4.10 | 2.30 | 5.05 | 3.90 | 3.32 | 3.18 |
| 5240 | MS | 4.10 | 2.30 | 5.05 | 3.90 | 3.32 | 3.18 |
| 5241 | MS | 2.89 | 1.68 | 7.68 | 6.25 | 4.50 | 3.50 |
| 5242 | MS | 5.52 | 3.08 | 6.14 | 4.15 | 2.69 | 4.11 |
| 5246 | MS | 2.40 | 4.76 | 2.91 | 1.92 | 2.12 | 5.87 |
| 5248 | MS | 1.69 | 1.01 | 2.44 | 2.40 | 2.37 | 1.34 |
| 5249 | MS | 2.99 | 2.15 | 7.17 | 3.79 | 2.76 | 2.66 |
| 5251 | MS | 1.89 | 1.23 | 3.63 | 2.37 | 2.81 | 1.47 |
| 5254 | MS | 2.42 | 2.35 | 2.73 | 1.91 | 1.68 | 1.69 |
| 5255 | MS | 8.92 | 1.53 | 2.97 | 2.76 | 2.84 | 3.31 |
| 5410 | MS | 2.18 | 2.93 | 2.65 | 1.16 | 1.38 | 3.17 |
| 5411 | MS | 1.92 | 1.42 | 3.82 | 1.90 | 1.69 | 4.32 |
| 5412 | MS | 2.63 | 1.72 | 2.08 | 2.02 | 2.17 | 2.97 |
| 5413 | MS | 7.06 | 3.84 | 2.93 | 3.49 | 3.79 | 5.62 |
| 5414 | MS | 2.51 | 1.50 | 2.69 | 4.00 | 3.95 | 2.13 |
| 5415 | MS | 3.67 | 0.91 | 1.33 | 2.33 | 5.02 | 2.59 |
| 5416 | MS | 4.39 | 3.81 | 2.42 | 1.66 | 1.76 | 7.06 |
| 5417 | MS | 5.30 | 6.53 | 17.28 | 4.51 | 4.08 | 7.07 |
| 5418 | MS | 3.50 | 3.04 | 3.26 | 3.05 | 2.56 | 2.42 |
| 5420 | MS | 2.88 | 2.28 | 3.69 | 3.73 | 5.83 | 3.28 |
| 5423 | MS | 2.65 | 1.72 | 2.25 | 4.14 | 2.19 | 2.43 |
| 5424 | MS | 3.01 | 2.20 | 2.23 | 2.26 | 2.53 | 2.04 |
| 5428 | MS | 2.97 | 2.38 | 4.86 | 2.78 | 2.78 | 2.61 |
| 5429 | MS | 3.89 | 2.49 | 4.18 | 8.13 | 6.00 | 5.87 |
| 5430 | MS | 3.12 | 2.31 | 3.23 | 4.16 | 10.76 | 2.28 |
| 5436 | MS | 6.39 | 3.49 | 4.33 | 3.10 | 2.15 | 3.95 |
| 5438 | MS | 2.31 | 2.18 | 2.55 | 2.92 | 3.52 | 1.63 |
| 5441 | MS | 2.28 | 1.83 | 4.69 | 7.07 | 2.82 | 2.37 |
| 5443 | MS | 1.98 | 1.44 | 3.39 | 1.96 | 1.65 | 1.72 |
| 5444 | MS | 9.93 | 4.45 | 10.92 | 7.19 | 10.55 | 7.15 |
| 5446 | MS | 2.29 | 1.66 | 2.89 | 3.43 | 2.89 | 3.87 |
| 5447 | MS | 1.54 | 1.79 | 1.66 | 4.00 | 2.27 | 1.03 |
| 5449 | MS | 6.02 | 2.59 | 8.69 | 5.17 | 4.51 | 4.27 |
| 5450 | MS | 1.46 | 1.12 | 1.64 | 1.55 | 1.25 | 1.41 |
| 5452 | MS | 1.51 | 1.03 | 1.46 | 1.98 | 1.60 | 2.18 |
| 5455 | MS | 3.42 | 3.15 | 2.39 | 1.68 | 1.32 | 1.64 |
| 5456 | MS | 3.69 | 2.42 | 8.09 | 2.16 | 1.15 | 1.99 |
| 5457 | MS | 7.33 | 3.88 | 6.72 | 8.80 | 6.62 | 9.37 |
| 5458 | MS | 2.70 | 1.46 | 3.07 | 4.00 | 2.04 | 1.58 |

TABLE 2-continued

| | | | | | | | |
|---|---|---|---|---|---|---|---|
| 5460 | MS | 2.96 | 2.39 | 11.87 | 2.98 | 2.00 | 2.91 |
| 5461 | MS | 2.54 | 1.69 | 2.14 | 3.67 | 2.49 | 2.53 |
| 5462 | MS | 2.66 | 1.54 | 2.64 | 3.60 | 2.11 | 1.75 |
| 5463 | MS | 5.56 | 5.11 | 2.69 | 2.81 | 2.02 | 6.63 |
| 5464 | MS | 2.87 | 4.94 | 4.60 | 3.35 | 2.90 | 4.17 |
| 5465 | MS | 3.30 | 2.28 | 4.12 | 4.35 | 2.91 | 2.31 |
| 5467 | MS | 4.45 | 4.12 | 8.18 | 3.34 | 3.83 | 3.18 |
| 5468 | MS | 2.97 | 4.81 | 2.98 | 4.77 | 3.27 | 9.22 |
| 5469 | MS | 5.98 | 3.49 | 12.13 | 6.41 | 4.21 | 6.56 |
| 5470 | MS | 3.74 | 1.91 | 2.56 | 4.03 | 2.43 | 3.65 |
| 5474 | MS | 2.38 | 1.32 | 8.74 | 1.61 | 1.99 | 1.24 |
| 5476 | MS | 2.90 | 1.90 | 8.02 | 3.17 | 3.05 | 3.42 |
| 5480 | MS | 2.63 | 1.95 | 4.92 | 3.44 | 2.86 | 6.04 |
| 5482 | MS | 3.15 | 2.27 | 1.68 | 1.99 | 2.67 | 2.29 |
| 5483 | MS | 6.70 | 5.78 | 5.27 | 6.72 | 9.71 | 5.43 |
| 5484 | MS | 3.57 | 2.92 | 6.31 | 5.50 | 3.56 | 3.57 |
| 5485 | MS | 8.44 | 3.22 | 6.95 | 3.52 | 3.36 | 6.29 |
| 5486 | MS | 3.72 | 3.93 | 14.71 | 3.60 | 2.90 | 2.70 |
| 5489 | MS | 1.96 | 1.23 | 2.37 | 1.54 | 1.23 | 1.38 |
| 9999 | MS | 3.46 | 2.79 | 1.86 | 2.84 | 2.00 | 3.46 |
| 5184 | OND | 2.47 | 1.06 | 3.08 | 2.25 | 1.47 | 1.91 |
| 5185 | OND | 0.97 | 0.81 | 1.39 | 0.88 | 1.01 | 0.80 |
| 5186 | OND | 1.67 | 2.09 | 2.69 | 3.29 | 2.03 | 1.12 |
| 5187 | OND | 1.55 | 1.82 | 2.61 | 1.41 | 1.40 | 1.24 |
| 5188 | OND | 6.94 | 1.99 | 2.77 | 2.01 | 1.74 | 1.82 |
| 5190 | OND | 1.02 | 0.61 | 0.70 | 1.13 | 1.13 | 0.73 |
| 5191 | OND | 1.10 | 0.77 | 2.20 | 1.74 | 1.32 | 1.00 |
| 5192 | OND | 0.86 | 0.98 | 1.71 | 1.73 | 1.47 | 0.92 |
| 5193 | OND | 1.62 | 1.25 | 1.31 | 0.83 | 0.76 | 0.79 |
| 5194 | OND | 2.25 | 1.40 | 2.22 | 1.43 | 1.89 | 1.29 |
| 5195 | OND | 3.58 | 2.69 | 4.77 | 2.63 | 1.90 | 2.00 |
| 5196 | OND | 1.85 | 1.60 | 4.68 | 1.62 | 1.15 | 2.30 |
| 5197 | OND | 2.18 | 0.98 | 0.87 | 1.78 | 1.67 | 1.09 |
| 5198 | OND | 2.01 | 1.82 | 2.16 | 2.62 | 2.45 | 1.28 |
| 5199 | OND | 1.36 | 1.27 | 0.88 | 1.21 | 0.90 | 0.92 |
| 5224 | OND | 1.02 | 1.01 | 0.96 | 1.17 | 1.54 | 0.94 |
| 5225 | OND | 5.99 | 5.58 | 6.17 | 5.69 | 4.24 | 6.04 |
| 5226 | OND | 1.63 | 1.50 | 1.34 | 2.22 | 1.58 | 0.92 |
| 5233 | OND | 2.07 | 0.91 | 0.94 | 3.43 | 3.87 | 1.31 |
| 5234 | OND | 0.83 | 0.69 | 1.41 | 1.30 | 2.46 | 1.02 |
| 5235 | OND | 1.66 | 2.08 | 1.91 | 1.64 | 1.31 | 1.59 |
| 5236 | OND | 2.64 | 1.57 | 2.92 | 2.32 | 2.89 | 1.52 |
| 5237 | OND | 3.98 | 2.09 | 5.76 | 5.22 | 4.89 | 2.90 |
| 5239 | OND | 6.65 | 2.03 | 1.62 | 1.35 | 1.15 | 2.38 |
| 5244 | OND | 1.45 | 1.05 | 1.63 | 1.34 | 1.41 | 1.11 |
| 5400 | OND | 1.20 | 0.76 | 1.42 | 1.58 | 1.72 | 1.27 |
| 5401 | OND | 1.87 | 1.26 | 2.26 | 2.41 | 2.22 | 1.03 |
| 5402 | OND | 5.87 | 2.78 | 3.57 | 2.01 | 2.29 | 5.43 |
| 5404 | OND | 1.66 | 1.23 | 1.70 | 1.67 | 1.72 | 1.31 |
| 5405 | OND | 1.61 | 0.78 | 1.65 | 1.31 | 1.48 | 1.09 |
| 5406 | OND | 1.22 | 1.13 | 1.20 | 1.48 | 1.39 | 1.15 |
| 5407 | OND | 2.56 | 1.86 | 4.59 | 2.92 | 2.41 | 2.45 |
| 5408 | OND | 6.28 | 4.30 | 2.70 | 4.75 | 5.79 | 4.52 |
| 5706 | OND | 1.56 | 1.07 | 2.39 | 2.05 | 1.53 | 1.02 |
| 5707 | OND | 2.30 | 1.42 | 2.37 | 2.05 | 2.06 | 1.40 |
| 5708 | OND | 2.21 | 1.45 | 2.96 | 2.29 | 2.20 | 2.03 |
| 5709 | OND | 2.38 | 1.94 | 2.60 | 2.01 | 2.04 | 2.11 |
| 5710 | OND | 4.22 | 2.55 | 1.87 | 2.47 | 3.33 | 4.25 |
| 5711 | OND | 1.13 | 0.88 | 0.89 | 1.02 | 1.16 | 0.99 |
| 5712 | OND | 0.83 | 0.93 | 1.25 | 1.25 | 1.14 | 0.66 |
| 5719 | OND | 2.29 | 2.21 | 2.99 | 3.26 | 3.29 | 1.73 |
| 5720 | OND | 1.22 | 1.39 | 1.25 | 2.58 | 2.12 | 1.45 |
| 5721 | OND | 1.74 | 1.02 | 1.11 | 1.46 | 1.92 | 1.45 |
| 5725 | OND | 1.90 | 1.81 | 1.60 | 2.12 | 2.23 | 2.16 |
| 5726 | OND | 12.33 | 3.51 | 8.29 | 6.42 | 6.88 | 7.51 |
| 5727 | OND | 6.29 | 3.85 | 6.68 | 6.45 | 6.20 | 3.31 |
| 5728 | OND | 1.28 | 0.93 | 1.38 | 1.54 | 1.26 | 0.98 |
| 5729 | OND | 2.85 | 0.98 | 2.96 | 1.69 | 1.73 | 1.97 |
| 5730 | OND | 1.50 | 1.18 | 1.59 | 1.56 | 1.89 | 1.13 |
| 5731 | OND | 2.01 | 1.66 | 1.57 | 2.05 | 2.24 | 1.88 |
| 5732 | OND | 1.65 | 1.37 | 2.20 | 3.20 | 2.79 | 1.31 |
| 5733 | OND | 4.02 | 2.51 | 4.41 | 4.23 | 2.78 | 1.35 |
| 5734 | OND | 1.38 | 1.05 | 1.55 | 1.29 | 1.19 | 1.29 |
| 5737 | OND | 1.83 | 1.76 | 4.04 | 2.38 | 1.98 | 1.56 |
| 5739 | OND | 2.56 | 1.91 | 3.92 | 3.14 | 3.30 | 2.25 |
| 5740 | OND | 2.16 | 1.59 | 3.26 | 2.13 | 1.81 | 2.29 |
| 5741 | OND | 2.26 | 1.54 | 2.71 | 1.77 | 2.53 | 3.29 |
| 6102 | OND | 4.96 | 3.69 | 5.00 | 8.59 | 14.54 | 3.86 |
| 8189 | OND | 1.76 | 1.16 | 2.33 | 1.82 | 1.79 | 1.51 |
| 8191 | OND | 1.62 | 1.57 | 2.79 | 3.87 | 3.06 | 2.22 |

Example 2

Anti-Sugar Based IgM Antibodies Predict the Development of Relapsing Remitting Multiple Sclerosis and a Subsequent Neurological Event After a First Neurological Event or CIS The value of selected serum IgM antibodies was evaluated in identifying those patients with a first acute neurological event (FNE) or clinically isolated syndrome (CIS), and who were suspected for having multiple sclerosis, that will (a) later be diagnosed as relapsing remitting MS (RRMS) by clinical follow up (i.e., clinically defined multiple sclerosis (CDMS)), or (b) will have a more active form of MS by rapidly progressing to RRMS.

Antibodies against the saccharides Glc($\alpha$1,4)Glc($\alpha$) (GAGA4), Glc($\alpha$1,6)Glc($\alpha$) (GAGA6), and $\alpha$-GlcNAc (GNa) were examined. The results in this example demonstrate that a high level of serum IgM antibodies against GAGA4 and GAGA6 at the time of a first acute neurological event predict those CIS patients who will develop CDMS in RRMS form, in comparison to MS-suspected patients that develop other neurological diseases (OND). These results also demonstrate that patients with high levels of anti-GAGA4 and or, anti-GNa IgM antibodies have increased risk for a second clinical attack within two years from disease onset. Anti-GAGA4, anti-GAGA6 and anti-GNa IgM antibodies thus can predict disease activity and identify CIS patients that develop CDMS more rapidly, within two years of first neurological event Frozen sera samples obtained from patients presenting for a diagnostic work-up of CIS (age 18-60) were retrospectively-prospectively tested. The study included patients that were followed for at least four years and were confirmed to have RRMS (n=44) according to Poser criteria (Poser et al. Ann Neurol. 13:227-31, 1983), and a control group of patients who presented as FNE or CIS but were eventually diagnosed as OND (n=44), including inflammatory neurological diseases (OIND, n=23) and other non-inflammatory neurological disease (ONIND, n=21). A schematic description of the study design is presented in FIG. 2. The RRMS and control groups were matched for gender composition, age and total IgM antibody level. Demographic and clinical characteristics of study population are shown in Table 3. Follow up data were available for 41 patients revealing whether they had an attack within 2 years from blood extraction, (i.e. First Neurological Event or CIS). Levels of anti-GAGA4, anti-GAGA6 and anti-GNa IgM were measured by immunoassay and normalized according to the levels of total IgM. Briefly, p-nitrophenyl derivatives of GAGA4, GAGA6 and GNa were covalently attached to the surface of a 96-well microtiter plate via a linker as previously described (U.S. Pat. No. 6,972,172, Schwarz M, et al. Glycobiology 13:749-54, 2003). Serum samples were diluted 1:1200 in 1% BSA in TBST, dispensed into the wells (50 μL per well) incubated for 30 min, then washed with PBST buffer. Bound antibodies were labeled with 50 μL of horseradish peroxidase (HRP)-conjugated goat anti-human IgM type-specific antibody, washed with PBST buffer, and 50 μL 3,3', 5,5'-tetramethylbenzidine (TMB) was added for detection. After 15 minutes the reaction was stopped with 50 μL 1% sulfuric acid solution and optical density (OD) was read at 450 nm with a Victor 1420 plate reader (Wallac, Turku, Finland).

Total IgM in each sera sample was measured as follows: goat anti-human IgM antibody (1 μg/mL in PBS) was adsorbed into a 96-well Maxisorp microtiter plate (Nunc, Denmark) overnight at room temperature. Serial dilutions of sera were added to the wells and incubated for 30 min at 27° C. Following washing of the plate in a PowerWasher™, biotinylated goat anti-human IgM was added for 30 min at 27° C. The immobilized immune complex was detected with Streptavidin-Europium and florescence readout. O.D.s measured for anti glycan antibodies were normalized for total IgM in serum samples, they were divided by RFU read out of total IgM assay.

Student's T-test was used to assess significance differences in anti glycan antibodies between RRMS and OND groups. A $\chi^2$ test was used for non-parametric variables. P-values of less than 0.05 were considered to be statistically significant.

TABLE 3

Demographic and clinical characteristics of study population

|  | RRMS | OND | ONIN | OIN |
| --- | --- | --- | --- | --- |
| N | 44 | 44 | 23 | 21 |
| Age, mean (SD), years | 37.6 (9.0) | 38.5 (9.5) | 36.5 (7.8) | 39.8 (11.1) |
| Women, n (%) | 38 (86) | 33 (75) | 17 (73) | 16 (76) |
| Total IgM, Mean (SD), RFU * 10$^6$ | 2.10 (0.80) | 1.94 (0.68) | 1.91 (0.71) | 1.93 (0.69) |

Identifying Patients That Will Later be Diagnosed as RRMS

Significantly higher levels of anti GAGA4 IgM and GAGA6 IgM antibodies (p=0.005, and p=0.01 respectively) were found in CIS patients who were eventually diagnosed with RRMS as opposed to OND, see Table 4 and FIG. 3. Although anti-GNa IgM antibodies were higher in CIS patients who were eventually diagnosed with RRMS as opposed to OND, the difference was not statistically significant. The OND sample set was used to set cut-off values of mean OD+2*SD for GAGA4 (0.53) and GAGA6 (0.21), for differentiation between OND and RRMS groups. Table 5 describes the diagnostic performance of each marker separately and in combination. (see also FIG. 2). Seventeen (17) patients out of 44 (38.6%) patients who were later diagnosed as RRMS were positive for GAGA4 or GAGA6; however, 42 out of 44 (95.4%) patients who where later diagnosed as OND where negative for both GAGA4 and GAGA6.

Identifying RRMS Patients Who Have a Second Attack Within 24 Months

Twenty six (26) patients of the 41 FNE or CIS patients who became RRMS had a second attack within 2 years from the day the blood was taken. The ability of the anti glycan antibodies to predict a next attack within 2 years was examined.

RRMS patients with higher levels (above median) vs. patients with lower levels (below median) of anti-GAGA4 and anti-GNa IgM antibodies went on significantly (16/20 (80%) vs. 10/21 (47%), and 17/20 (80%) vs. 9/21 (43%), $\chi^2$ test, p=0.025, odds ratio 4.4, Confidence Interval (CI) 95% 1.6-11.8, and odds ratio 7.5 CI 95% 2.4-23.8, respectively) to have further attacks within 2 years of their first neurological events. No significance was found regarding GAGA6. See Table 6.

FIGS. 4A and B describe ROC curves for differentiating between FNE or CIS patients who became RRMS and had a second attack within 2 years from RRMS patients that did not have second attack within 2 years based on anti-GNa and anti-GAGA4 IgM antibodies. Although anti-GNa IgM antibody levels did not significantly differ between RRMS and OND patients, they differentiated between patients who become RRMS and had a second relapse with in 2 years and patients who become RRMS but did not had a second attack within 2 years. By using cutoff value of 0.55 (anti-GNa IgM O.D./RFU*1000000) 60% sensitivity at 93% specificity can be achieved. Anti-GAGA4 IgM in conjunction with Anti-GAGA6 IgM have higher sensitivity (39%), higher specificity (95%) and higher prediction value (89%) for distinguishing between CIS patients who will evolve to RRMS, and those who turn out to have OND. In addition, higher levels of IgM antibodies to the GAGA4 and GNa epitopes, seen at the CIS stage patients, predict patients that will convert rapidly to CDMS (within 2 years).

TABLE 4

Anti-sugar IgM antibody levels in RRMS and OND patients

|  | Signal intensity, O.D./RFU * 10$^6$ Mean (SD) | |
| --- | --- | --- |
| Glycans | RRMS (n = 44) | OND (n = 44) |
| Glc(α1,4)Glc(α) | 0.44 (0.30)** | 0.30 (0.11) |
| Glc(α1,6)Glc(α) | 0.15 (0.10)* | 0.11 (0.05) |
| α-GlcNAc | 0.50 (0.34) | 0.40 (0.23) |

*p < 0.05 versus CD
**p = 0.005 versus CD

TABLE 5

Differentiation between RRMS patients and OND patients based on anti-GAGA4, anti-GAGA6, and combined score.

| Anti glycan antibodies (cutoff) | Sensitivity (%) | Specificity (%) | Positive predictive value (%) | Negative predictive Value (%) | Efficiency (%) |
|---|---|---|---|---|---|
| Anti-GAGA4 (0.53) | 34.1 | 90.9 | 78.9 | 58.0 | 62.5 |
| Anti-GAGA6 (0.21) | 22.7 | 97.7 | 90.0 | 55.3 | 59.8 |
| Positive for Anti-GAGA4 or Anti-GAGA6 | 38.6 | 95.6 | 89.5 | 60.9 | 67.0 |

TABLE 4

Association between anti-GAGA4 IgM, and anti-GNa IgM antibody levels and having a second attack within 2 years, in FNE or CIS patients who become RRMS.

| | Number of RRMS patient who had a second attack within 2 years/Total patients | | |
|---|---|---|---|
| Antibody | Patients with antibodies levels below median | Patients with antibodies levels above median | Odds ratio (CI 95%) |
| Anti-GAGA4 IgM* | 10/21 (47%) | 16/20 (80%) | 4.4 (1.5–11.8) |
| Anti-GAGA6 IgM | 11/21 (52%) | 15/20 (75%) | 3.3 (1.3–8.0) |
| Anti-GNa IgM* | 9/21 (43%) | 17/20 (85%) | 7.5 (2.4–23.8) |

*p = 0.025, $\chi^2$ test

Example 3

Diagnosis of RRMS or Rapid CDMS in a Patient Presenting With a FNE or CIS

A patient presents with symptoms of Multiple Sclerosis at his first Neurological Event (FNE) or with CIS. A serum sample is removed from the patient an tested for the presence of an anti-α-GlcNAc (GNa) antibody, an anti-Glc(α1,4)Glc(α) IgM (GAGA4) antibody and an anti-Glc(α1,6)Glc(α) (GAGA6) antibody. The levels of the antibodies in the test sample are compared to a cut-off value represent the level of antibodies in a control sample whose MS status is known. The cut-off values to progress to RRMS or to progress rapidly to CDMS can be determined based on the antibody levels in patients with known RRMS, Rapid CDMS or OND as describe at Example 2. A FNE or CIS subject is considered likely to progress to RRMS or to progress rapidly to CDMS if levels of the antibodies are greater than the pre-defined cut-off value.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of predicting whether a subject with a First Neurological Event (FNE) will develop relapsing remitting multiple sclerosis (RRMS) or whether a subject with a FNE will develop other neurological disease (OND), the method comprising:
   providing a blood sample from a subject at FNE;
   detecting in said blood sample an anti-Glc(α1,4)Glc(α) (GAGA4) IgM isotype antibody and an anti-Glc(α1,6) Glc(α) (GAGA6) IgM isotype antibody;
   comparing the levels of said antibodies in said blood sample to levels of said antibodies in individuals with OND; and
   differentiating an FNE subject predicted to develop RRMS from an FNE subject predicted to develop OND by detection of a higher level of said antibodies in said blood sample compared to an OND level of said antibodies.

2. The method of claim 1, wherein said subject with a First Neurological event (FNE) has symptoms of a Clinically Isolated Syndrome (CIS) suggestive of multiple sclerosis.

3. The method of claim 1, wherein said subject is a female.

4. The method of claim 1, wherein said subject is a male.

5. The method of claim 1, wherein said antibody is detected using a glycan containing a Glc(α1,4)Glc(α) (GAGA4) or a Glc(α1,6)Glc(α) (GAGA6) linkage.

6. The method of claim 1, wherein said antibody is detected using an oligosaccharide that includes a glycan containing a Glc(α1,4)Glc(α) (GAGA4) or a Glc(α1,6)Glc(α) (GAGA6) linkage.

7. The method of claim 1, wherein said antibody is detected using a polymer that includes a glycan containing a Glc(α1,4)Glc(α) (GAGA4) or a Glc(α1,6)Glc(α) (GAGA6) linkage.

8. The method of claim 1, wherein said polymer is a polysaccharide.

9. The method of claim 7, wherein said polymer is naturally occurring.

10. The method of claim 7, wherein said polymer is a synthetic polymer.

* * * * *

UNITED STATES PATENT AND TRADEMARK OFFICE
CERTIFICATE OF CORRECTION

PATENT NO. : 7,906,291 B2
APPLICATION NO. : 11/345190
DATED : March 15, 2011
INVENTOR(S) : Nir Dotan et al.

Page 1 of 1

It is certified that error appears in the above-identified patent and that said Letters Patent is hereby corrected as shown below:

Column 9, lines 1-3, "(α)-(Ga2Ga), Glc(α1,3)Glc(α)-Ga3Ga, Glc(α1,6)Glc(α)-Ga6Ga, Glc(α1,4)Glc(α)-Ga4Ga, α-Glc-Ga, and α-GlcNAc-GNa." should read:

--(α) (Ga2Ga), Glc(α1,3)Glc(α) (Ga3Ga), Glc(α1,6)Glc(α) (Ga6Ga), Glc(α1,4)Glc(α) (Ga4Ga), α-Glc (Ga), and α–GlcNAc (GNa).--

Signed and Sealed this
Twenty-sixth Day of June, 2012

David J. Kappos
*Director of the United States Patent and Trademark Office*